(12) United States Patent
Falco

(10) Patent No.: US 7,314,047 B2
(45) Date of Patent: Jan. 1, 2008

(54) HEARING PROTECTION DEVICE

(75) Inventor: Robert Falco, Indianapolis, IN (US)

(73) Assignee: Cabot Safety Intermediate Corporation, Newark, DE (US)

(*) Notice: Subject to any disclaimer, the term of this patent is extended or adjusted under 35 U.S.C. 154(b) by 0 days.

(21) Appl. No.: 10/352,336

(22) Filed: Jan. 27, 2003

(65) Prior Publication Data
US 2003/0172938 A1 Sep. 18, 2003

Related U.S. Application Data

(60) Provisional application No. 60/351,762, filed on Jan. 25, 2002.

(51) Int. Cl.
A61C 5/14 (2006.01)

(52) U.S. Cl. ........................ 128/864; 128/865

(58) Field of Classification Search ........ 128/864–868; 181/130, 135
See application file for complete search history.

(56) References Cited

U.S. PATENT DOCUMENTS

| D195,322 S | 5/1963 | Hill | |
|---|---|---|---|
| 4,314,553 A * | 2/1982 | Westerdal | 128/864 |
| 4,671,265 A | 6/1987 | Andersson | |
| D298,356 S | 11/1988 | Falco | |
| 4,867,149 A * | 9/1989 | Falco | 128/864 |
| 4,936,411 A | 6/1990 | Leonard | |
| 5,113,967 A * | 5/1992 | Killion et al. | 181/132 |
| 5,668,354 A | 9/1997 | Falco | |
| 5,727,566 A * | 3/1998 | Leight | 128/857 |
| 5,819,745 A | 10/1998 | Mobley et al. | |
| D402,752 S | 12/1998 | Falco | |
| D414,260 S | 9/1999 | Conner | |
| D427,304 S | 6/2000 | Magidson et al. | |
| D436,164 S | 1/2001 | Foslien | |
| 6,241,041 B1 * | 6/2001 | Leight | 181/135 |
| 6,286,622 B1 | 9/2001 | Tiemann | |
| D466,995 S * | 12/2002 | Knauer et al. | D24/106 |
| D472,627 S | 4/2003 | Falco | |
| 6,568,394 B2 | 5/2003 | Falco | |
| 2004/0045558 A1 * | 3/2004 | Taylor et al. | 128/864 |

FOREIGN PATENT DOCUMENTS

| EP | 0 244 979 | 11/1987 |
|---|---|---|
| EP | 0 847 736 | 6/1998 |

OTHER PUBLICATIONS

International Search Report; PCT/US03/02412; Jan. 8, 2004 European Search Report; EP 847736A1; Feb. 26, 1998.

* cited by examiner

Primary Examiner—Michael A. Brown
(74) Attorney, Agent, or Firm—Cantor Colburn LLP

(57) ABSTRACT

An earplug is provided including an elongate stem component having a first end and an opposite second end, a first flange disposed on the stem proximate the first end, a second flange disposed on the stem adjacent the first flange, a third flange disposed on the stem adjacent the second flange, opposite the first flange, and proximate the second end, a rib support element formed on the first, second, and third flanges, wherein, the first, second, and third flanges comprise generally hemispherical flange elements extending from the stem in a direction toward the second end such that a generally annular space is formed between inner surfaces of the first, second, and third flanges and the stem, and wherein the rib support element is formed on the inner surfaces.

16 Claims, 26 Drawing Sheets

HEARING PROTECTION DEVICE

CROSS REFERENCE TO RELATED APPLICATIONS

This application is related to and claims the benefit of U.S. Provisional Patent Application No. 60/351,762 filed Jan. 25, 2002, which is herein incorporated by reference in its entirety.

BACKGROUND OF THE INVENTION

1. Field of the Invention

The present invention relates broadly to hearing protective devices and is more specifically directed to a resilient polymeric multiple flange earplug useful as a hearing protector.

2. The Prior Art

The use of hearing protection and noise attenuating devices is known, and various types of devices are available for this purpose. Such devices include, but are not limited to, earmuffs, semi-aural devices, and earplugs.

Earplugs are generally preferred for continuous use over longer periods of time. Slow recovery foam earplugs such as those disclosed in U.S. Pat. No. Reissue 29,487 are considered to be comfortable and have been shown to deliver high in-field noise protection at all frequencies. U.S. Pat. No. 5,203,352 to Gardner, Jr. also discloses a hearing protective earplug utilizing a polymeric foam.

Earplugs comprising a resilient soft polymeric material formed about a component member are also known as disclosed, for example, in U.S. Pat. No. 4,867,149 to Falco herein incorporated by reference in its entirety. Therein, at least three resilient soft polymeric hemispherically shaped flanges are formed about a component member. The flanges are generally rearwardly directed, circular cross-sectioned, skirt members of relatively thin uniform thickness, spaced apart along the component member. A first flange extends from a nose end of the component member toward a rear-end. The successive flange elements increase serially in diameter with respect to a diameter of the first flange. A diameter of the stalk member is selected to provide an annular space between an inner surface of the flange elements and a surface of the polymeric material of the component member, the space being of sufficient dimension as to allow the flange to collapse and compress into and occupy the space upon insertion of the earplug into the ear canal, thus attenuating sound.

Flanged resilient soft polymeric stemmed earplugs, as described in Falco, are considered to provide comfort, sound attenuation, styling, and universal sizing and to allow easy insertion and cleaning. However, the flanges of such earplugs have been known to yield or wrinkle undesirably upon insertion into a user's ear thus effecting the attenuation and comfort provided by the earplugs. Further, such earplugs have been known to conform to the curvatures of the ear canal thus reducing comfort for the user.

Accordingly, a flanged resilient soft polymeric stemmed earplug is desired in which wrinkling of the flanges upon insertion into an ear is reduced and yet comfort, good attenuation, and ease of use is maintained.

SUMMARY OF THE INVENTION

An earplug is provided including an elongate stem component having a first end and an opposite second end, a first flange disposed on the stem proximate the first end, a second flange disposed on the stem adjacent the first flange, a third flange disposed on the stem adjacent the second flange, opposite the first flange, and proximate the second end, a rib support element formed on the first, second, and third flanges, wherein, the first, second, and third flanges comprise generally hemispherical flange elements extending from the stem in a direction toward the second end such that a generally annular space is formed between inner surfaces of the first, second, and third flanges and the stem, and wherein the rib support element is formed on the inner surfaces.

The above-discussed and other features and advantages of the present invention will be appreciated and understood by those of ordinary skill in the art from the following detailed description and drawings.

BRIEF DESCRIPTION OF THE DRAWINGS

Referring now to the drawings wherein like elements are numbered alike in the several FIGURES.

DESCRIPTION OF THE PREFERRED EMBODIMENT

Figure 1:
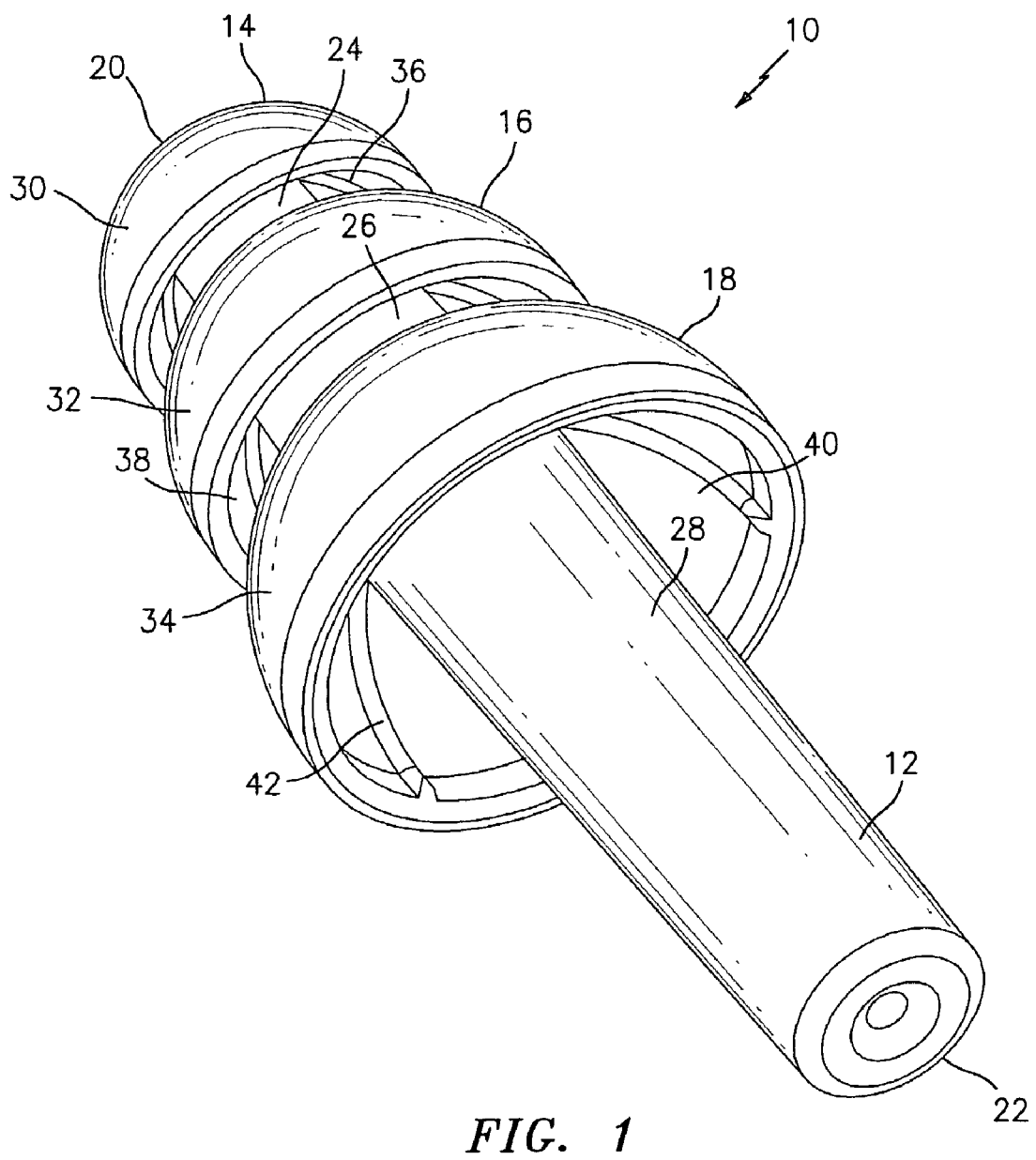
FIG. 1 is a bottom perspective view of an EARPLUG in one embodiment of the invention.
Figure 2:
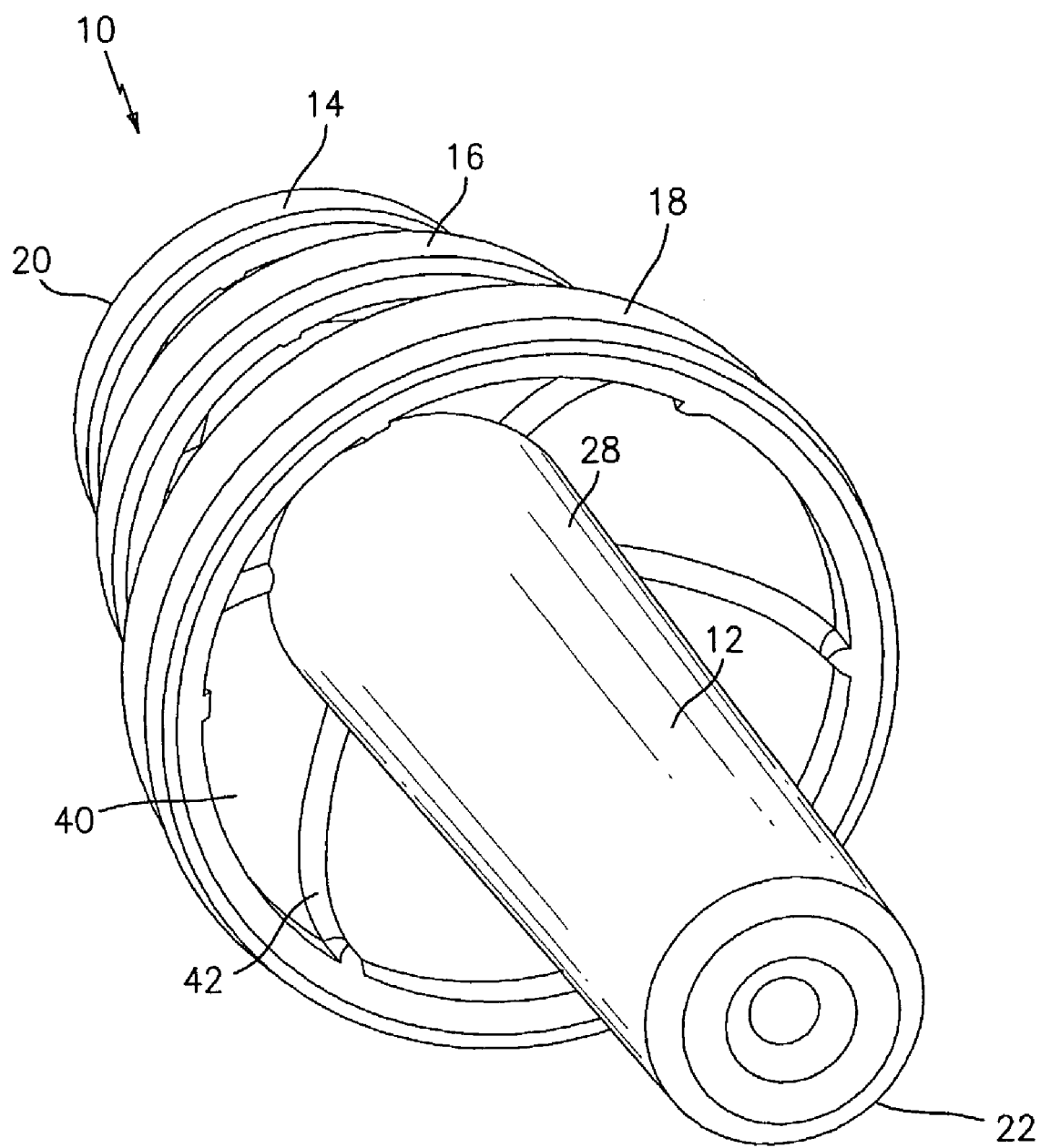
FIG. 2 is another bottom perspective view thereof.

FIGS. 1–6 show an earplug 10 in a first embodiment including a stem 12 and a first flange 14, a second flange 16, and a third flange 18 each disposed on the stem 12.

First flange 14 is disposed at a first end 20 of earplug 10. Second flange 16 is disposed adjacent first flange 14 and spaced therefrom in a direction of a second end 22 of earplug 10, second end 22 being opposite first end 20. Third flange 18 is disposed adjacent second flange 16 and spaced therefrom in the direction of second end 22.

Stem 12 is a generally cylindrical longitudinal member comprising a first portion 24 located beneath first flange 14, a second portion 26 located beneath second flange 16, and a third portion 28 located beneath third flange 18 and extending to second end 22. A diameter of first portion 24 is smaller than the respective diameters of second and third portions 26 and 28. The diameter of third portion 28 may taper slightly toward second end 22.

Figure 3:
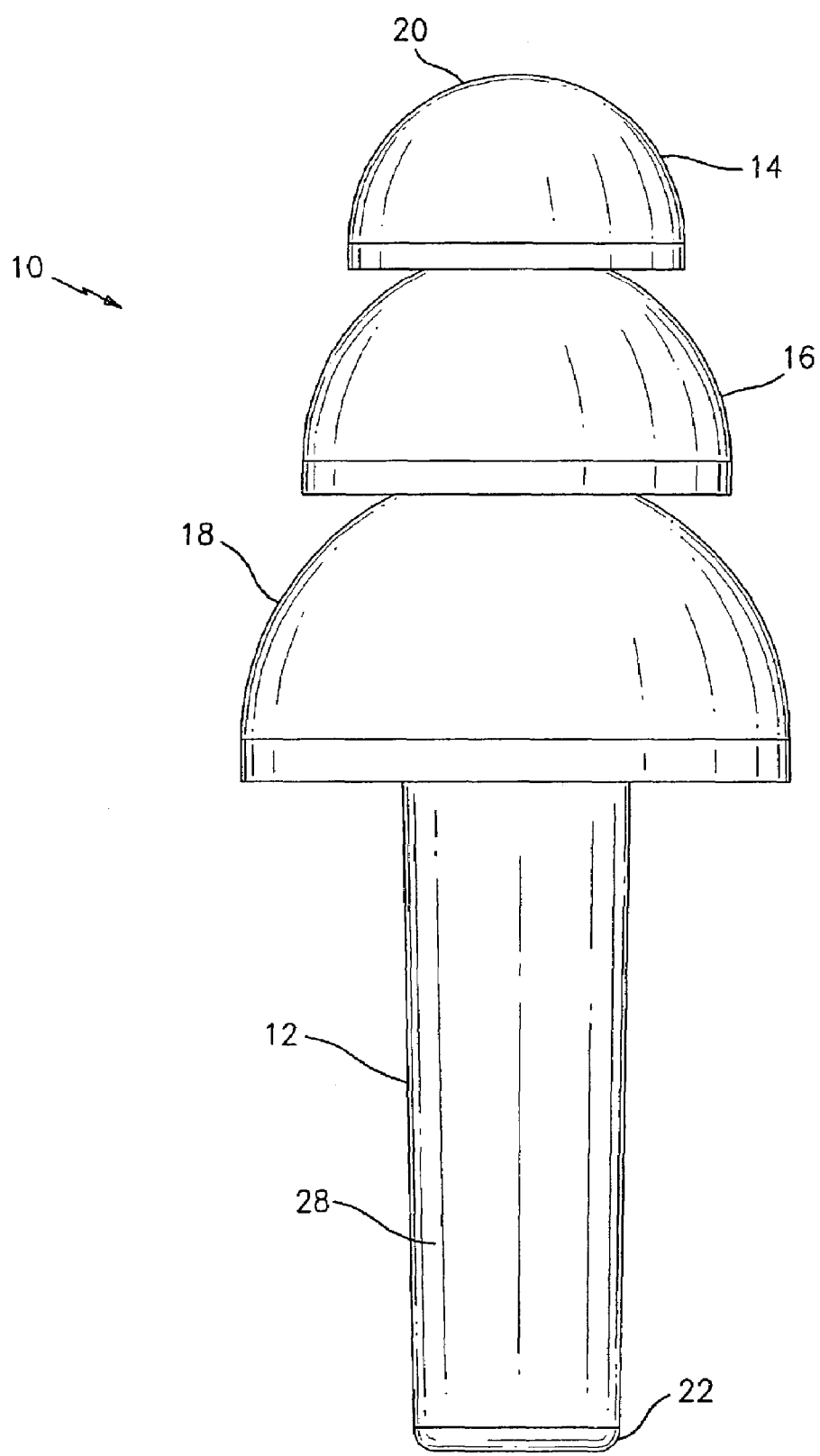
FIG. 3 is a side elevational view thereof.
Figure 3A:
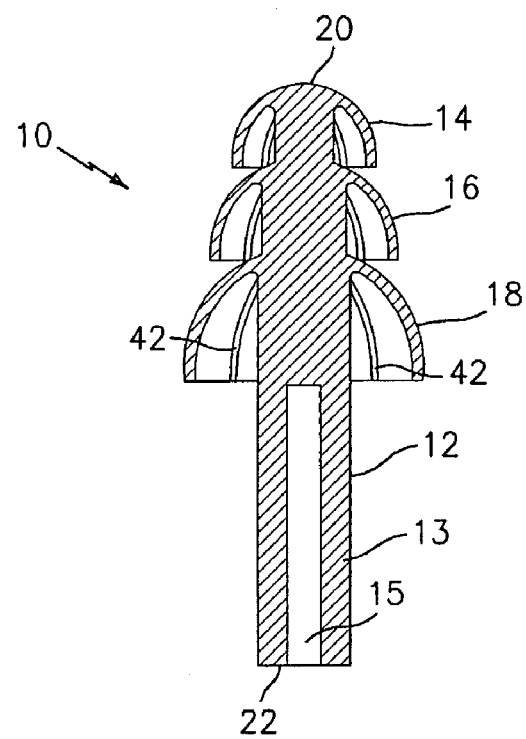
FIG. 3A is a cross-sectional view thereof.
Figure 3B:
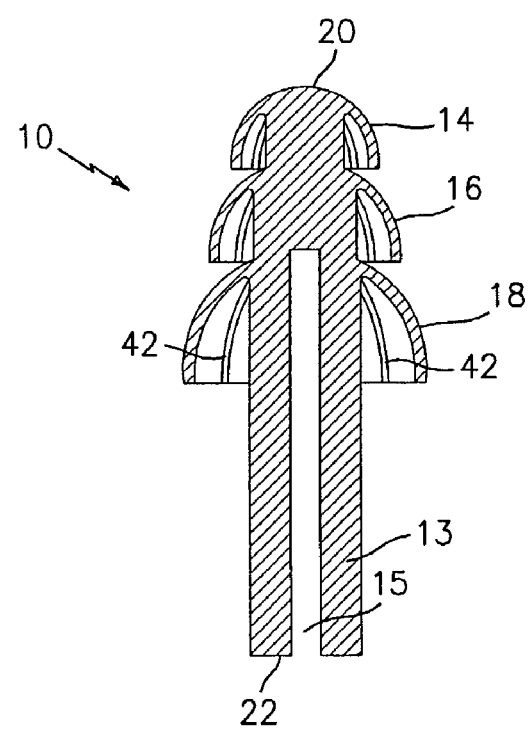
FIG. 3B is another cross-sectional view thereof.
Figure 4:
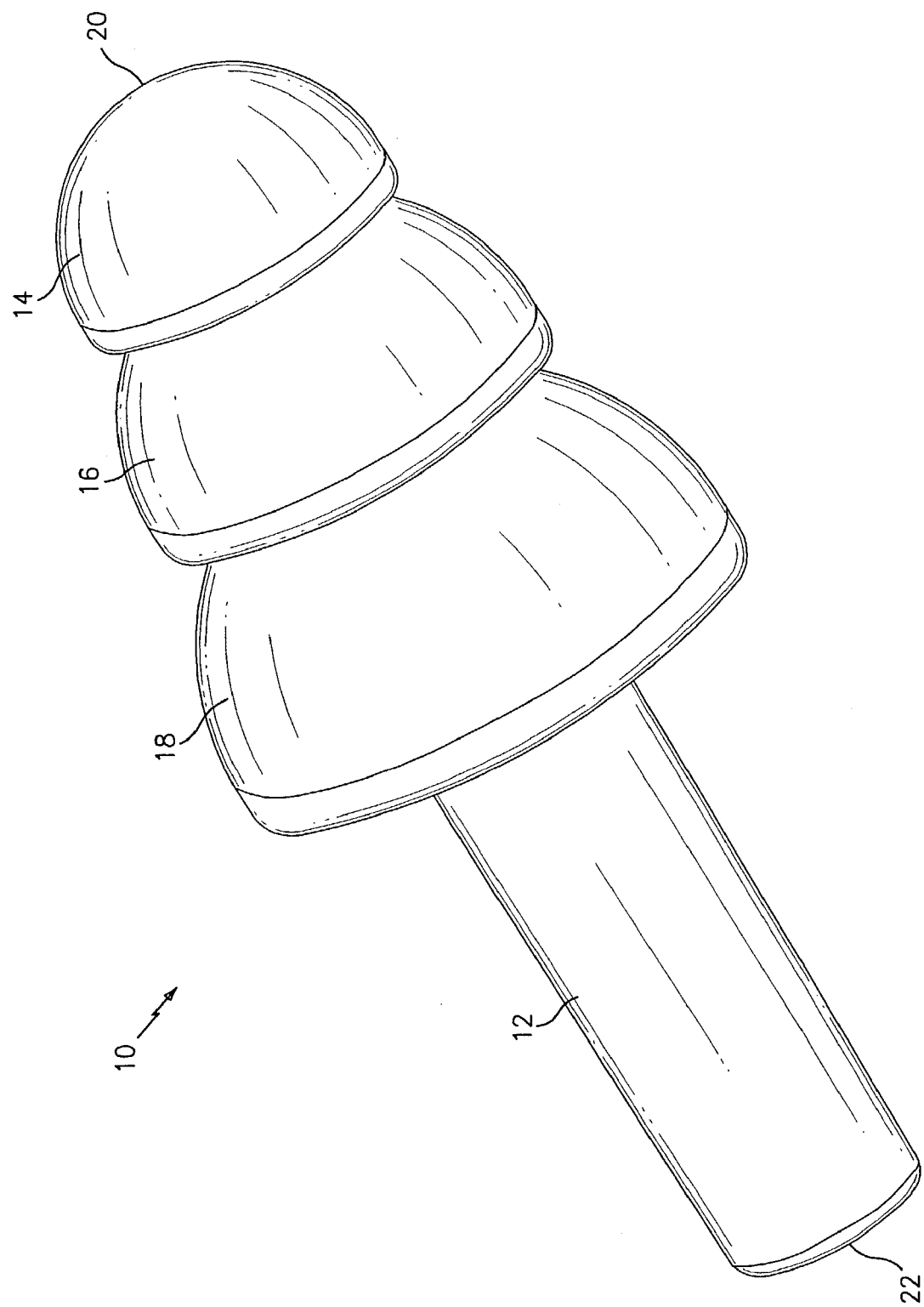
FIG. 4 is a top perspective view thereof.
Figure 5:
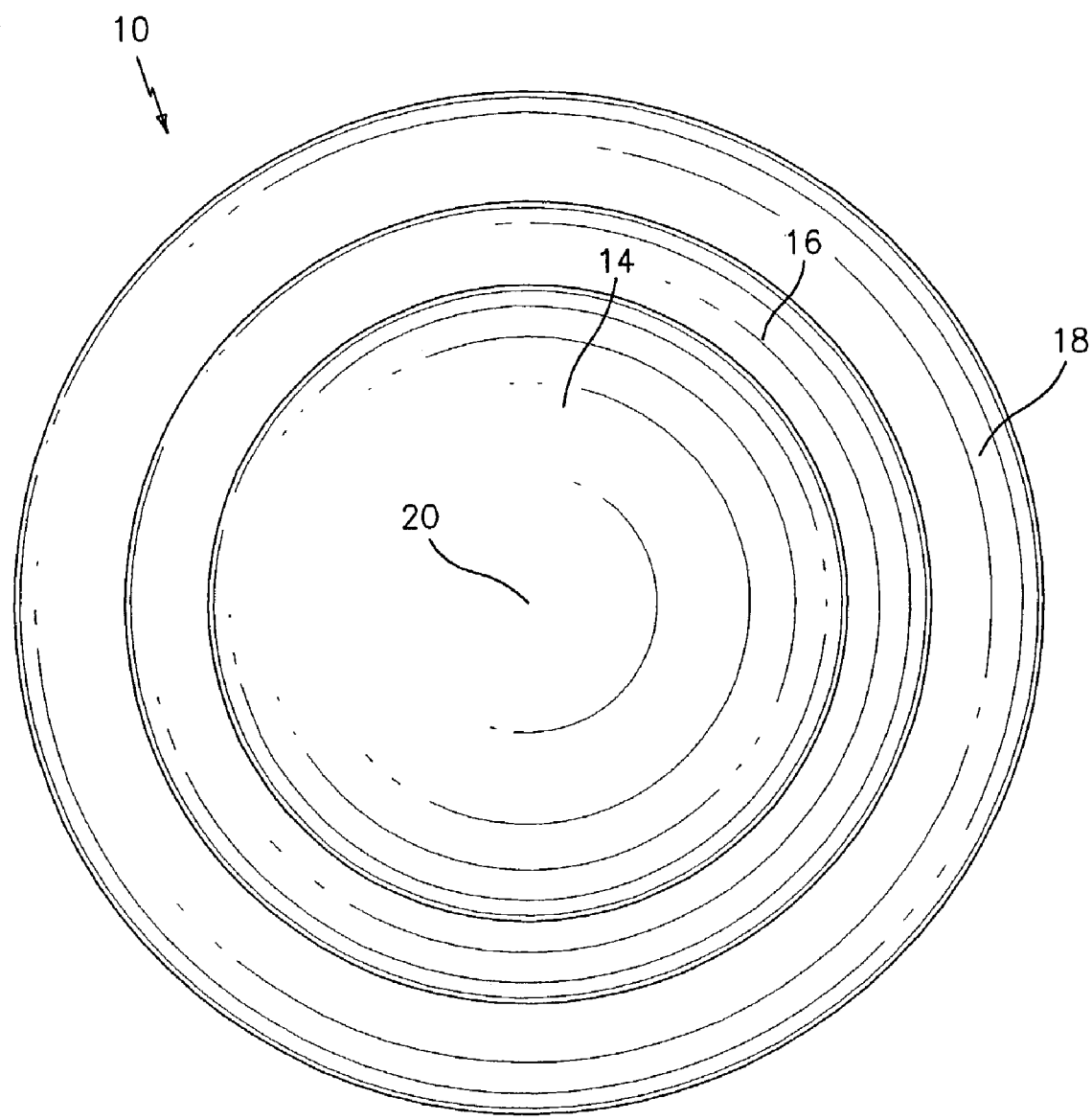
FIG. 5 is a top plan view thereof.

Referring now particularly to FIGS. 3a and 3b, stem 12 comprises a cavity 13 formed therein for receiving a cylindrical component 15. The component 15 is entirely encapsulated within stem 12. However, it is noted but not shown that alternatively, component 15 may extend from second end 22. Component 15 is made of rigid or semirigid material and extends from second end 22 towards first end 20. In one embodiment, as shown in FIG. 3a, component 15 extends to a point approximately equal to an end of third flange 18 most proximate second end 22 of earplug 10. In still another embodiment, as shown in FIG. 3b, component 15 extends to a point beneath second flange 16. Component 15 comprises any suitable stiffing agent such as a cylindrical peg, a cord, etc.

First, second, and third flanges, 14, 16, and 18, extend outwardly and rearwardly in semi-hemispherical fashion from stem 12 thereby defining annular spaces between the flanges and stem 12. A diameter of first flange 14 is smaller than a diameter of second flange 16 which is smaller than a diameter of third flange 18. First, second, and third flanges, 14, 16, and 18, are compressible into the annular spaces when earplug 10 is inserted into an ear canal of a user to provide an acoustical sealing therewith.

First, second, and third flanges 14, 16, and 18 include first, second, and third outer surfaces 30, 32, and 34, respectively. Additionally, first, second, and third flanges 14, 16, and 18 include first, second, and third inner surfaces 36, 38, and 40, respectively.

Figure 6:
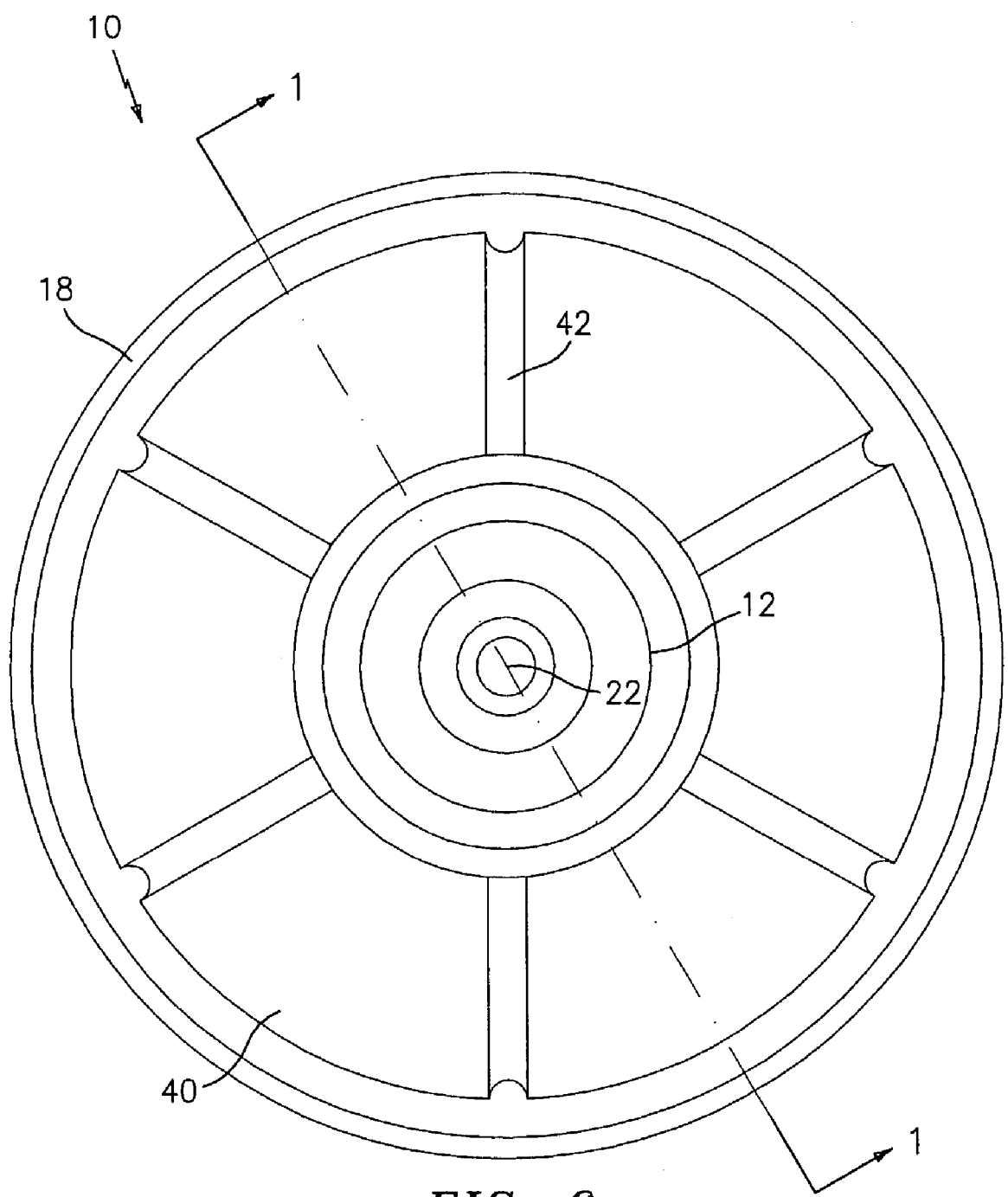
FIG. 6 is a bottom plan view thereof.
Figure 7:
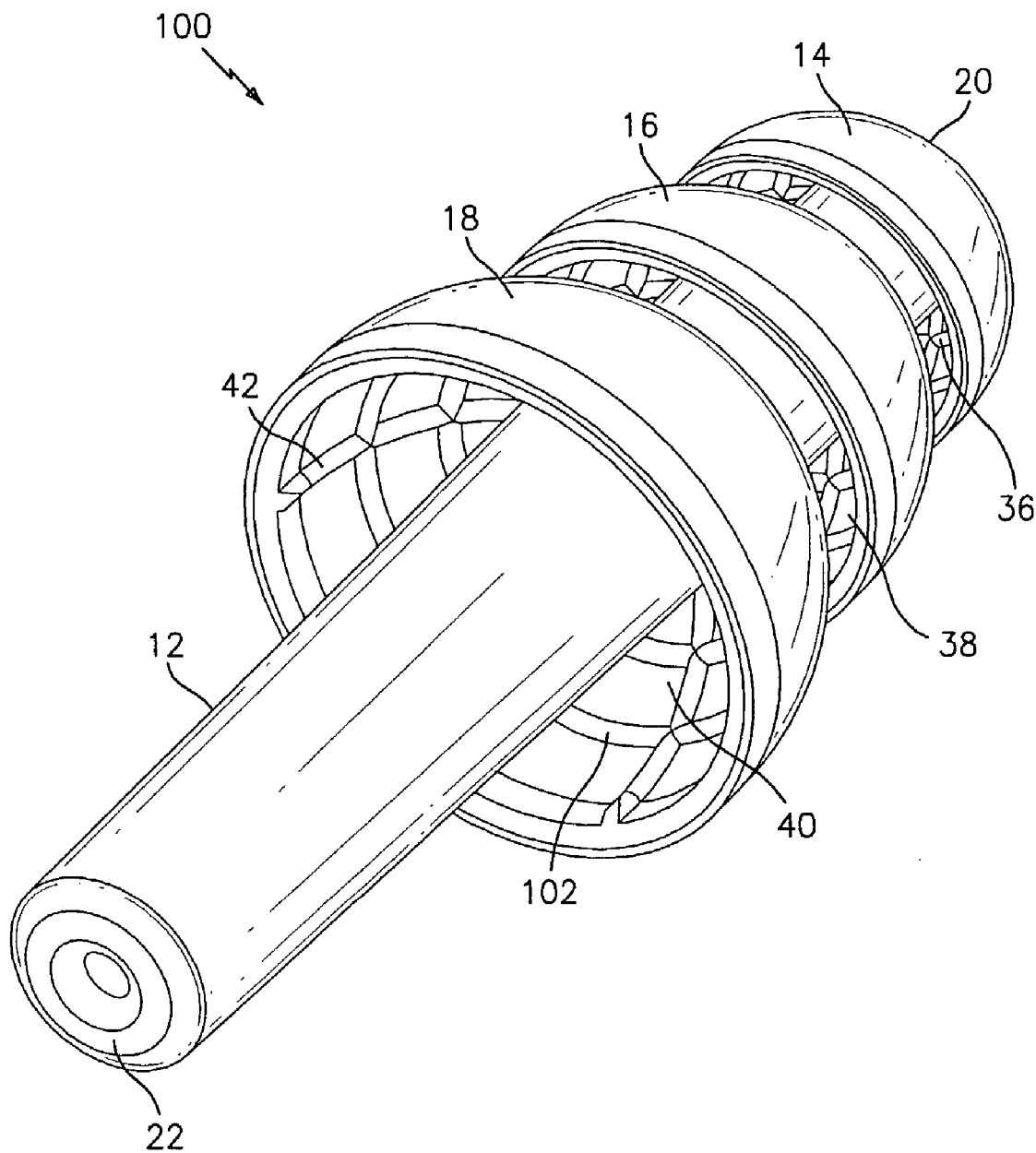
FIG. 7 is a bottom perspective view of an earplug in another embodiment of the invention.
Figure 8:
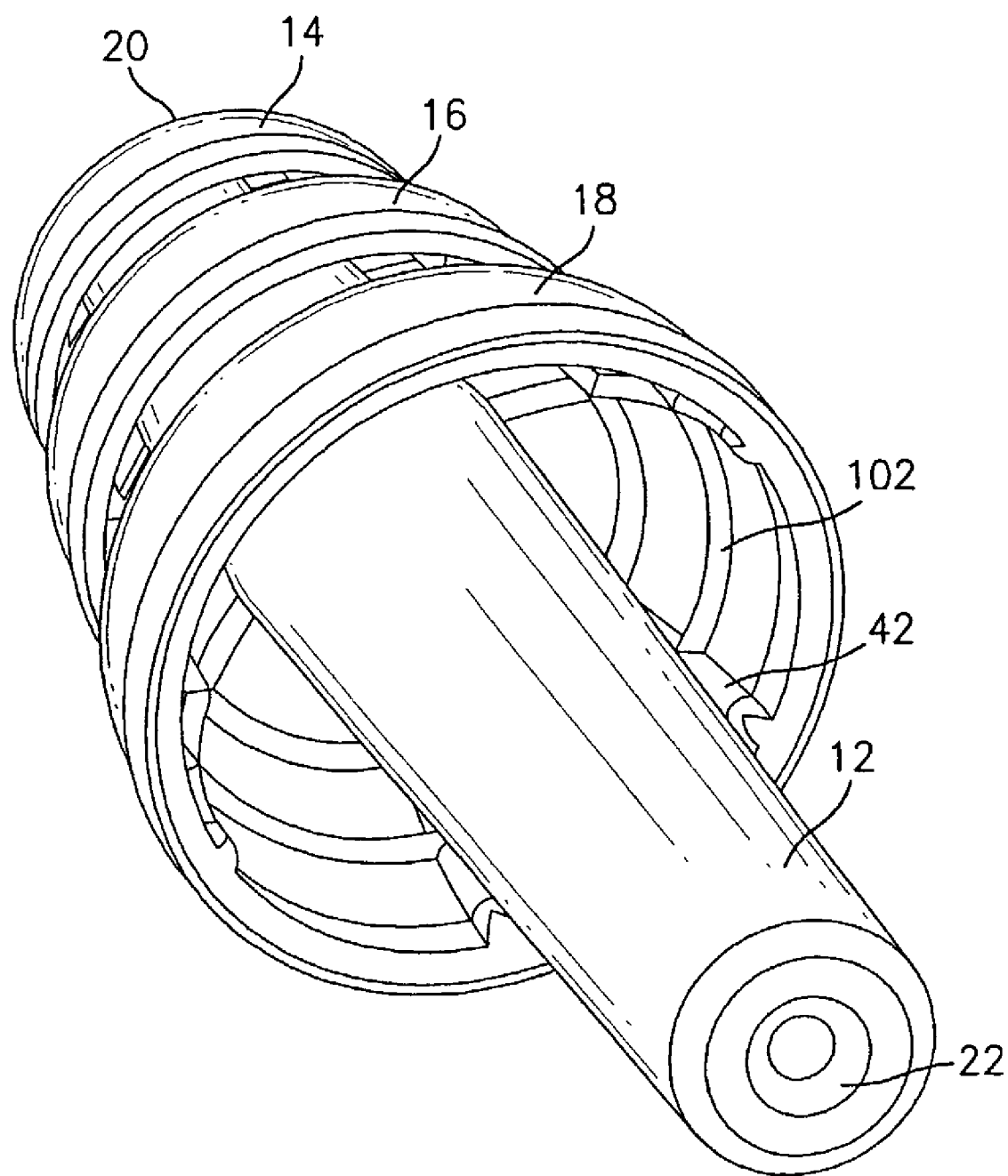
FIG. 8 is another perspective view thereof.
Figure 9:
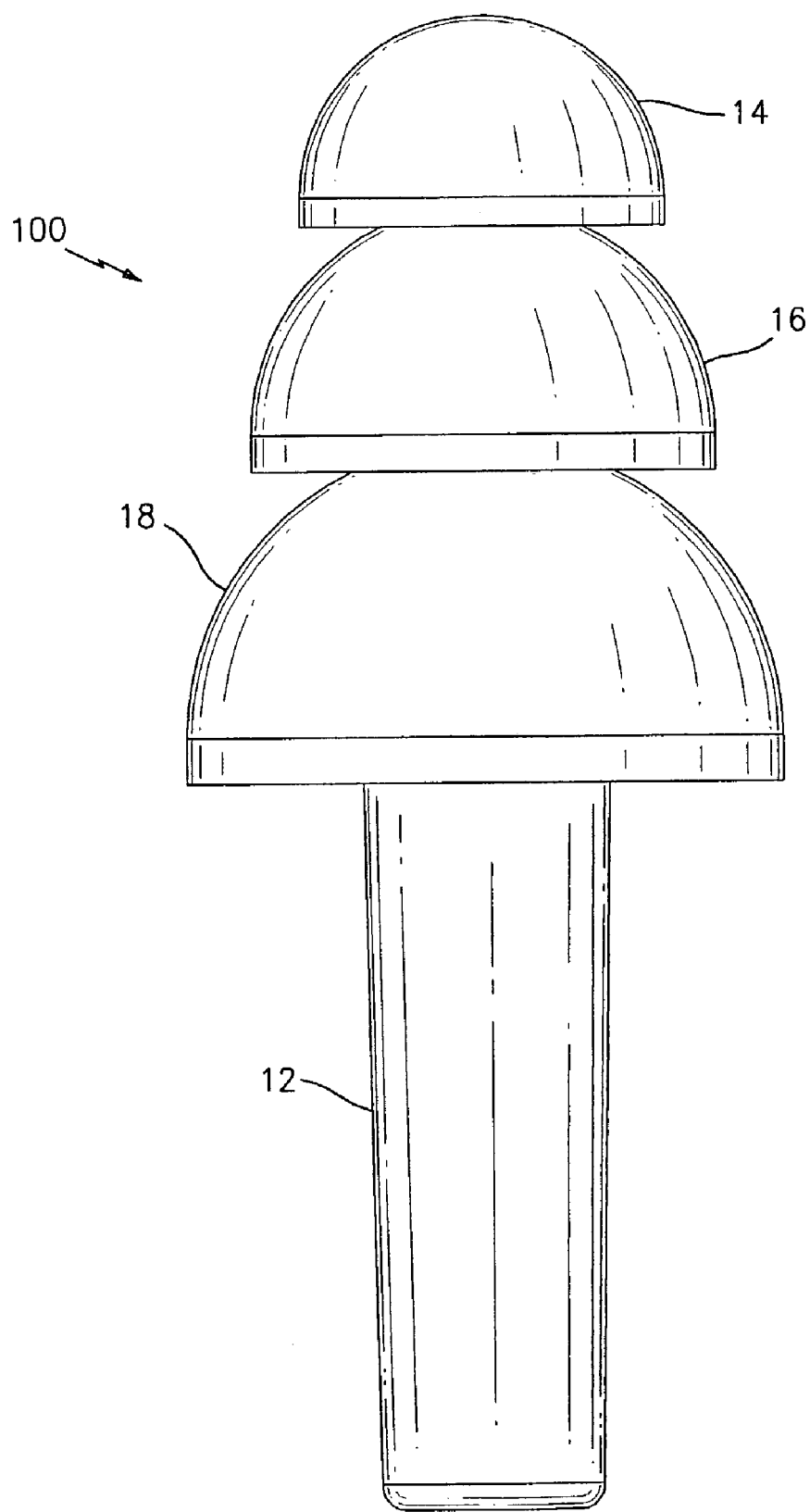
FIG. 9 is a side elevational view thereof.
Figure 10:
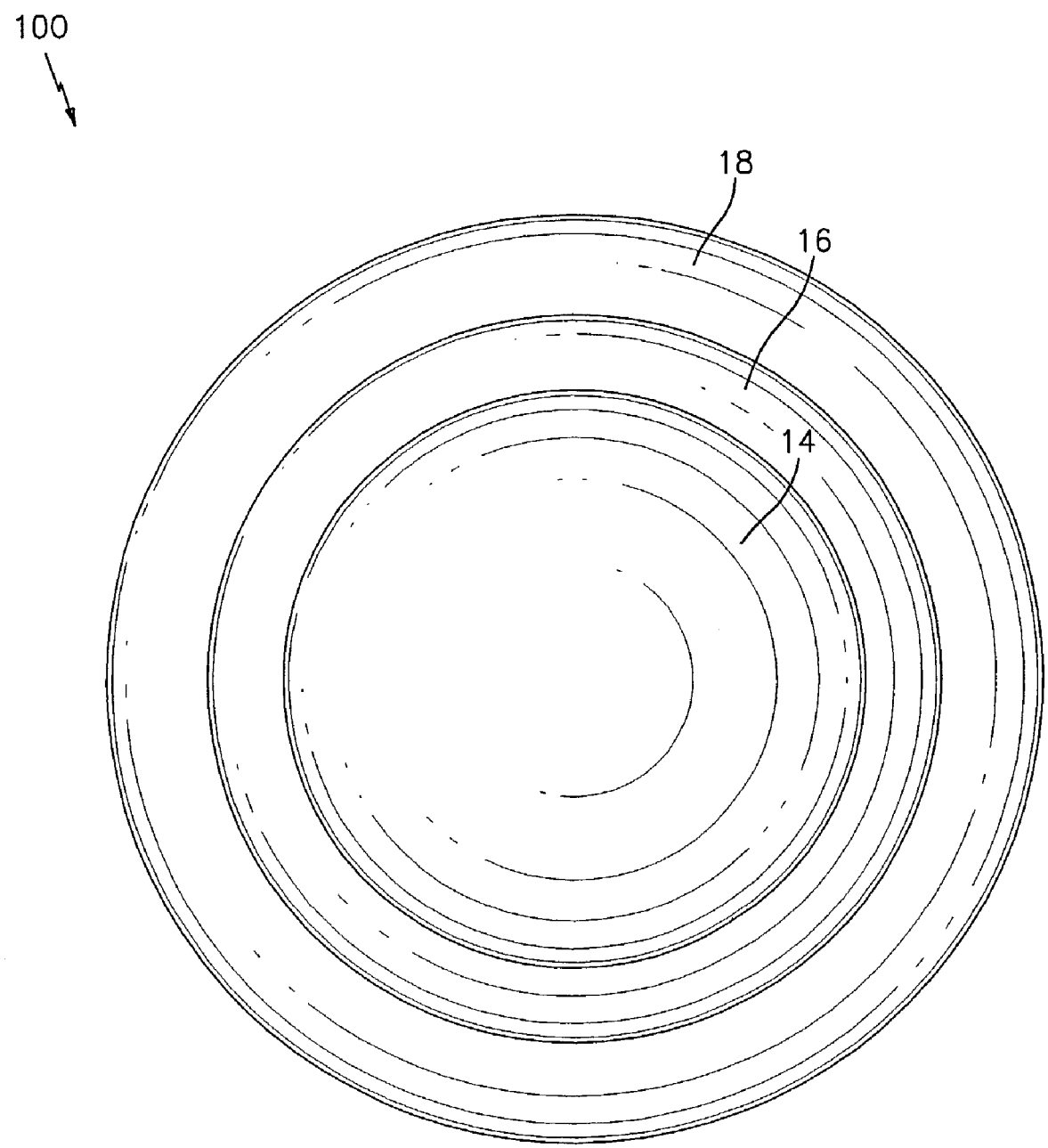
FIG. 10 is a top plan view thereof.
Figure 11:
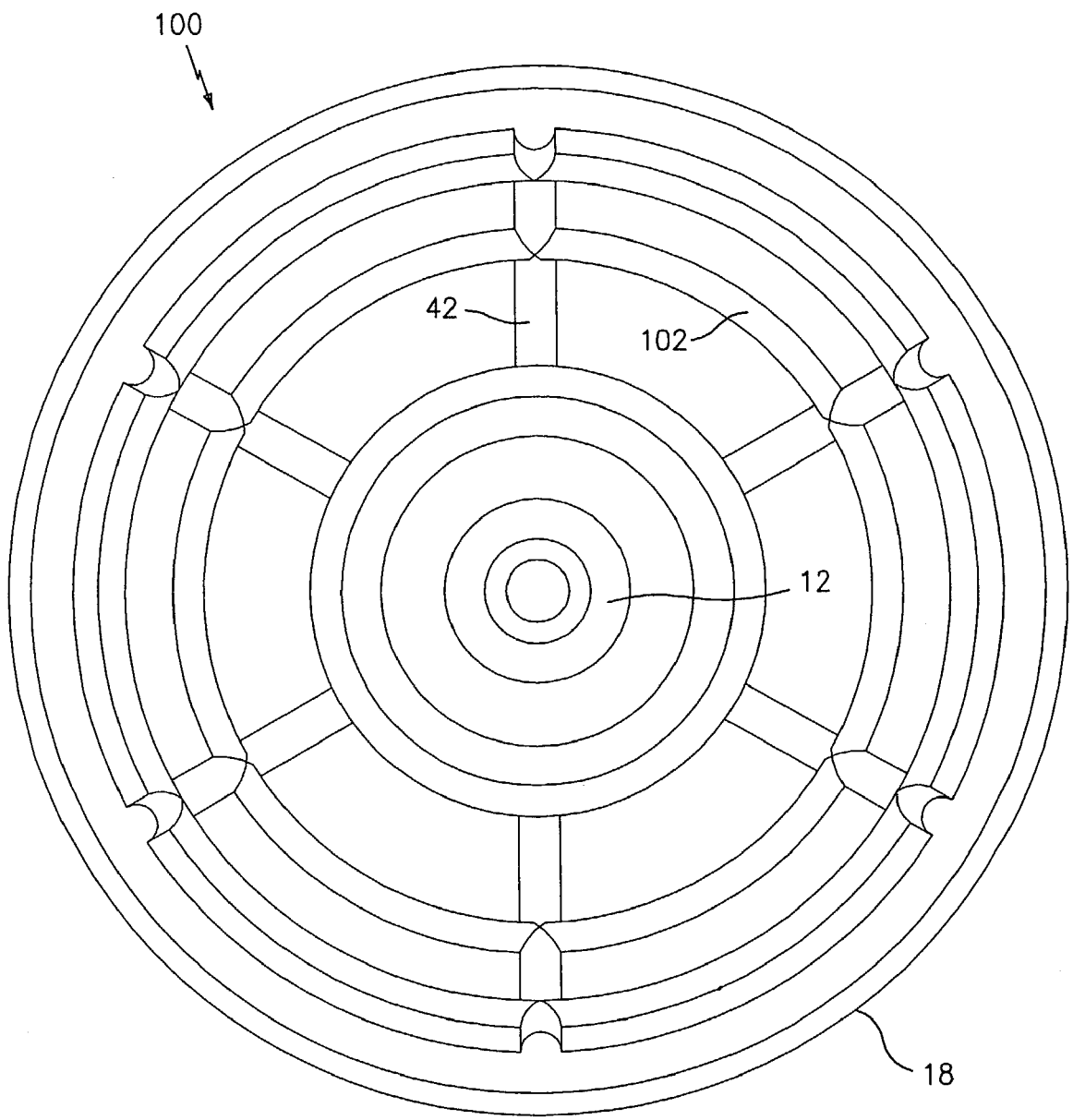
FIG. 11 is a bottom plan view thereof.
Figure 12:
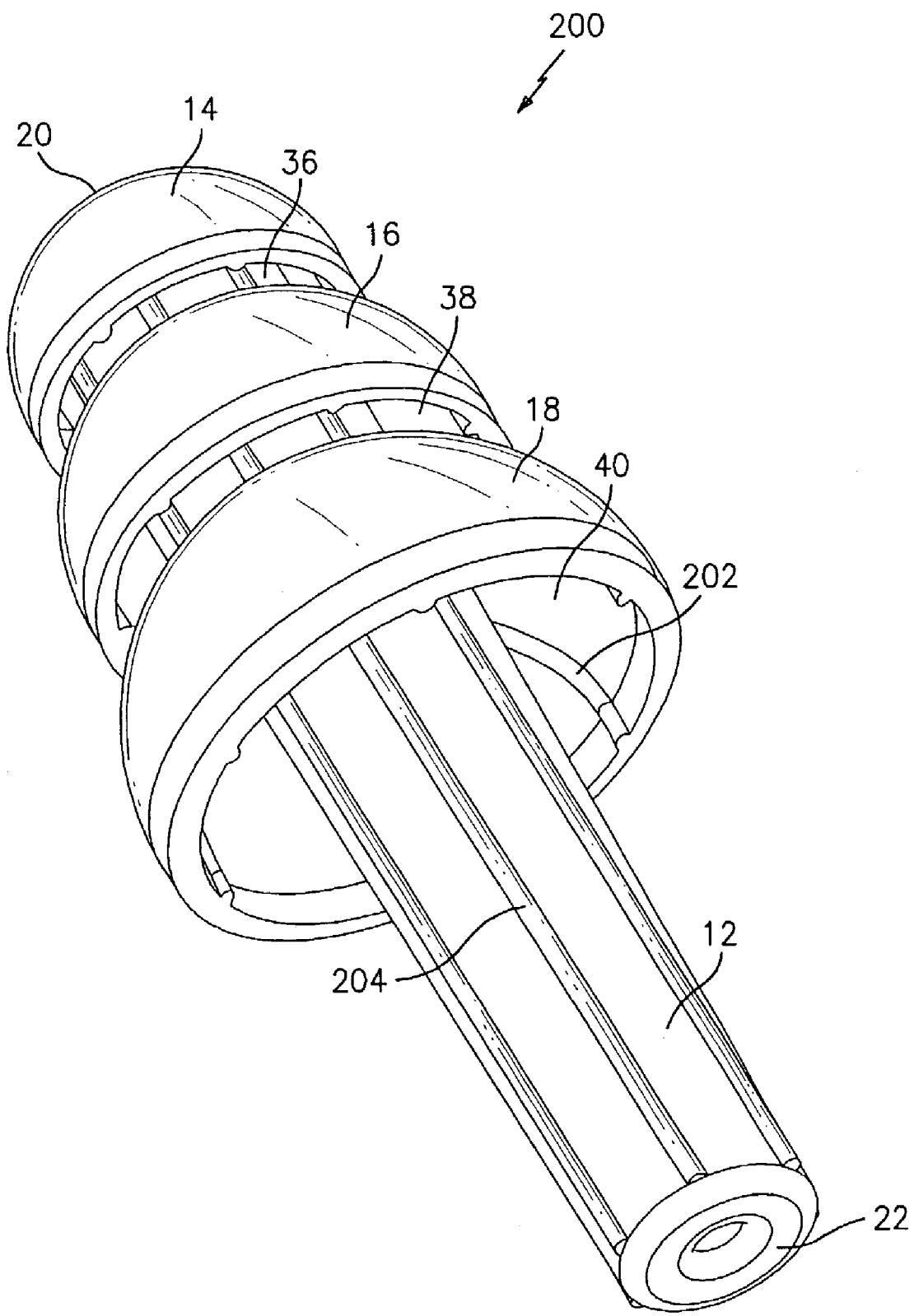
FIG. 12 is a bottom perspective view of an earplug in another embodiment of the invention.
Figure 13:
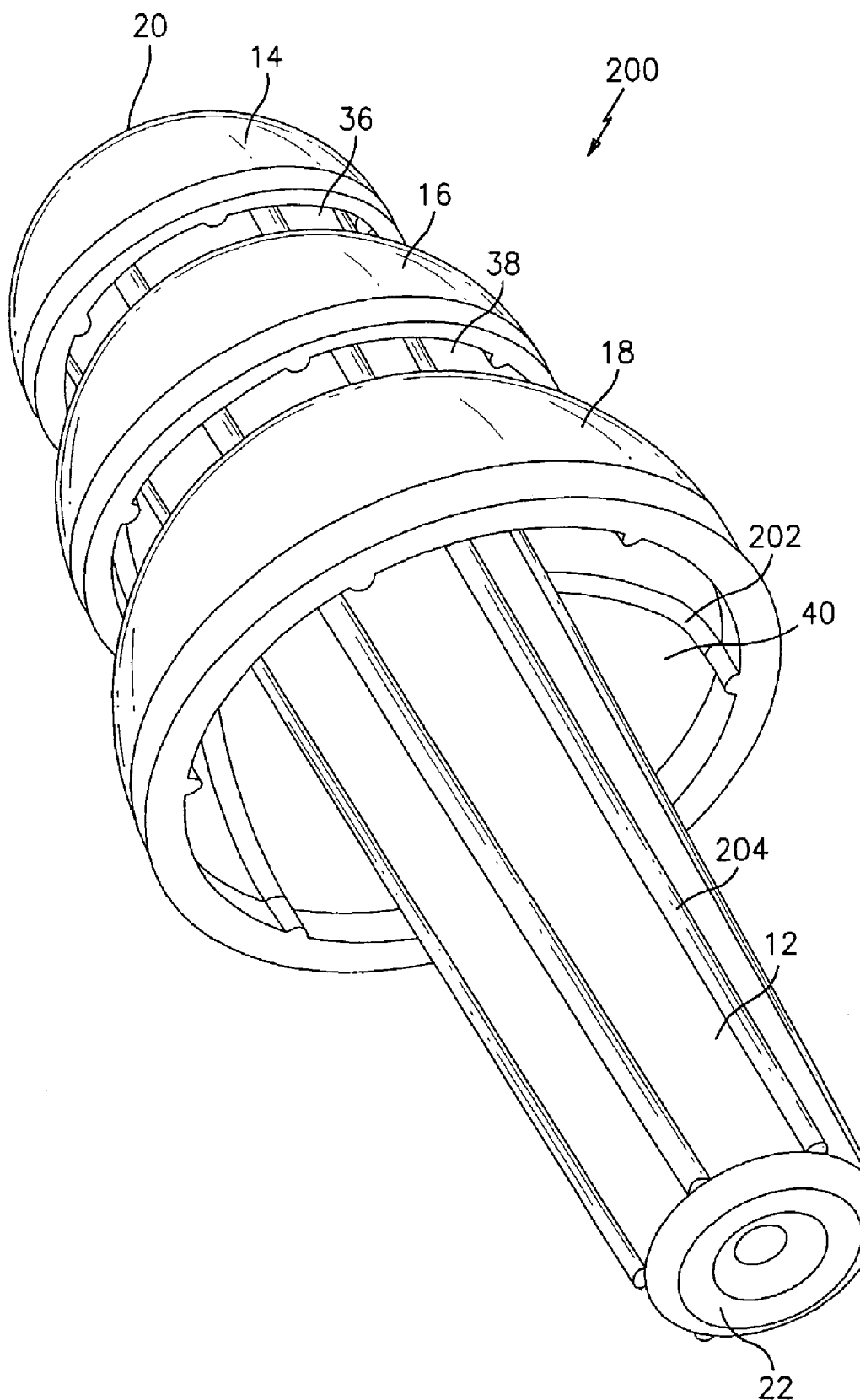
FIG. 13 is a another bottom perspective view thereof.
Figure 14:
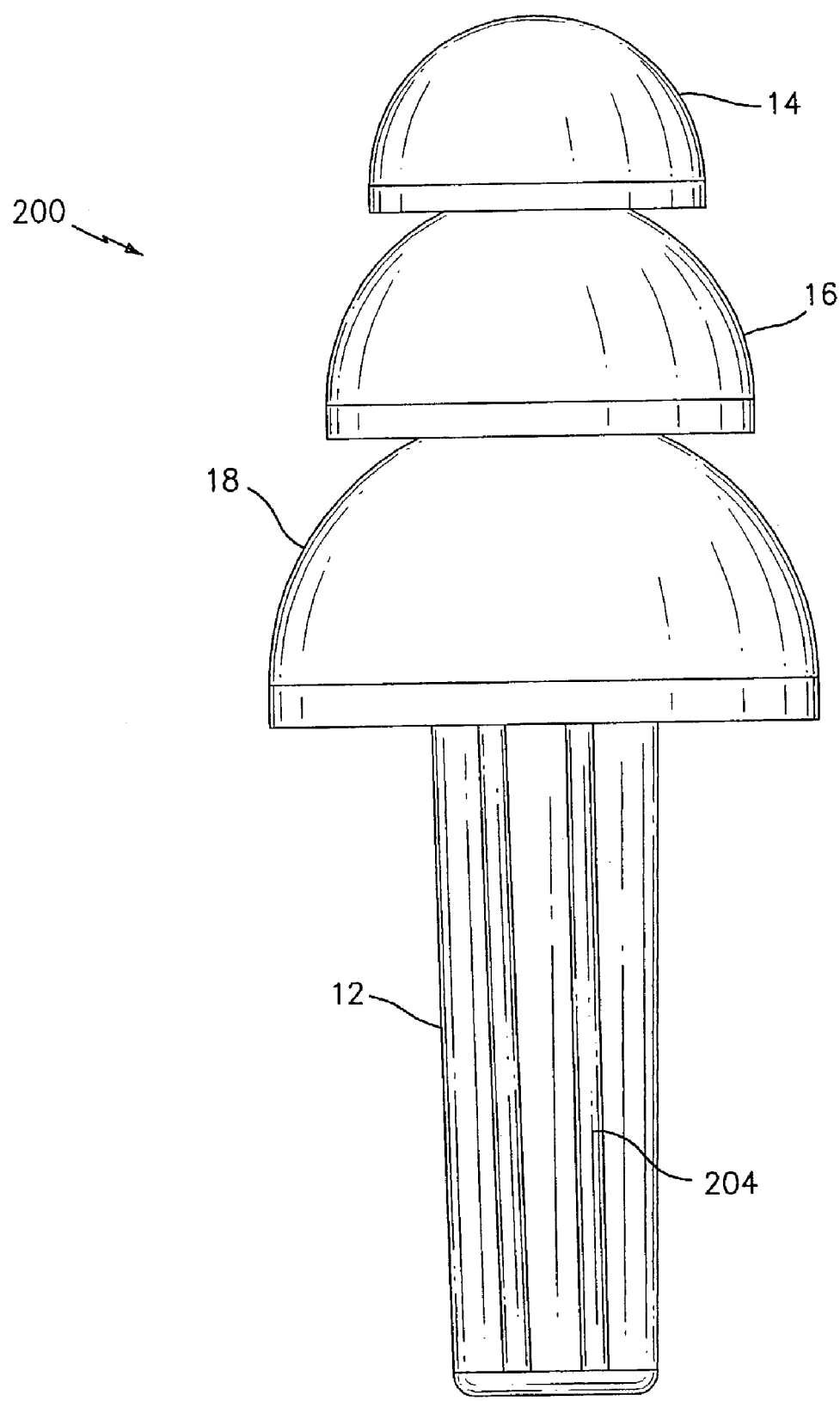
FIG. 14 is a side elevational view thereof.
Figure 15:
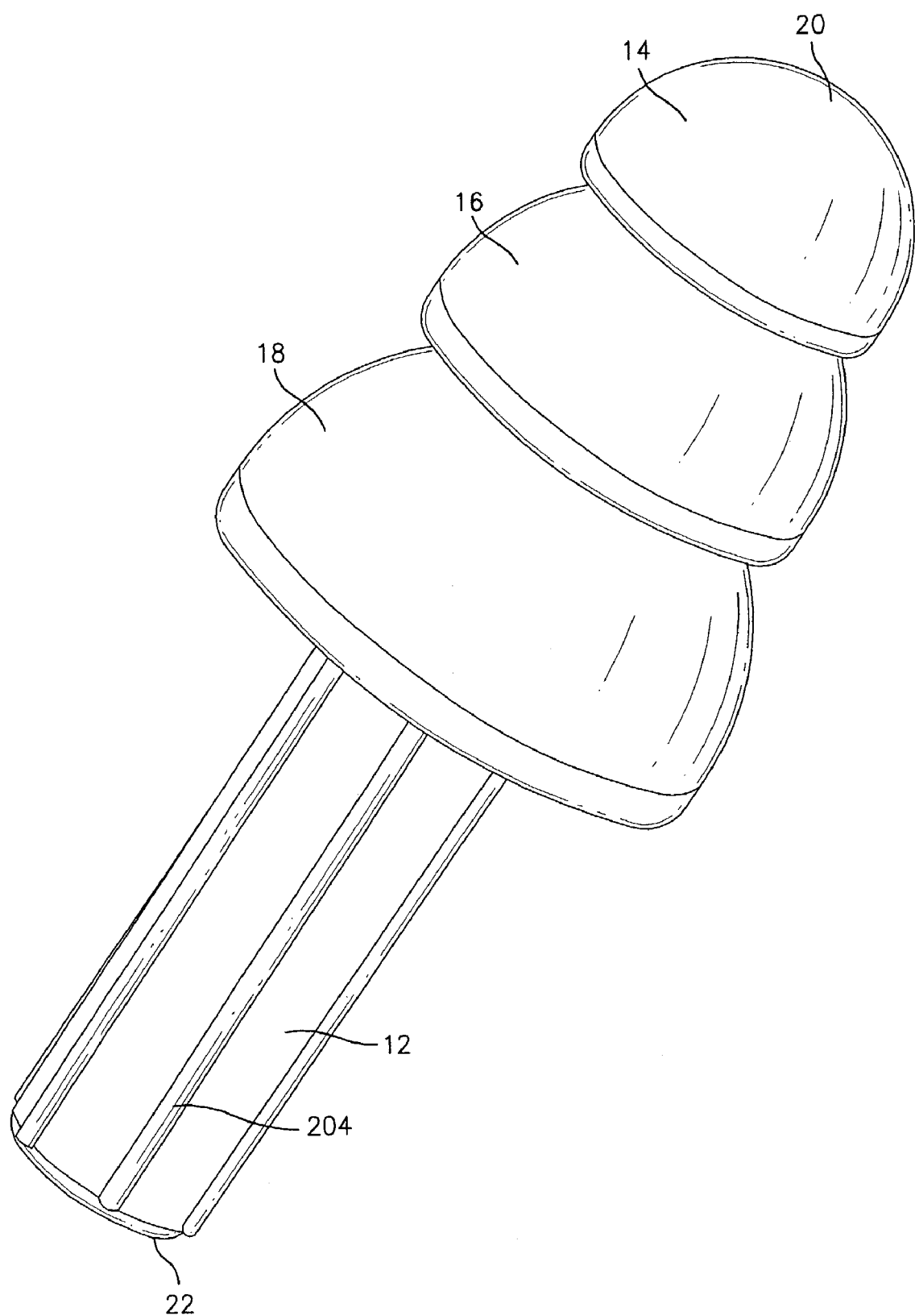
FIG. 15 is a top perspective view thereof.
Figure 16:
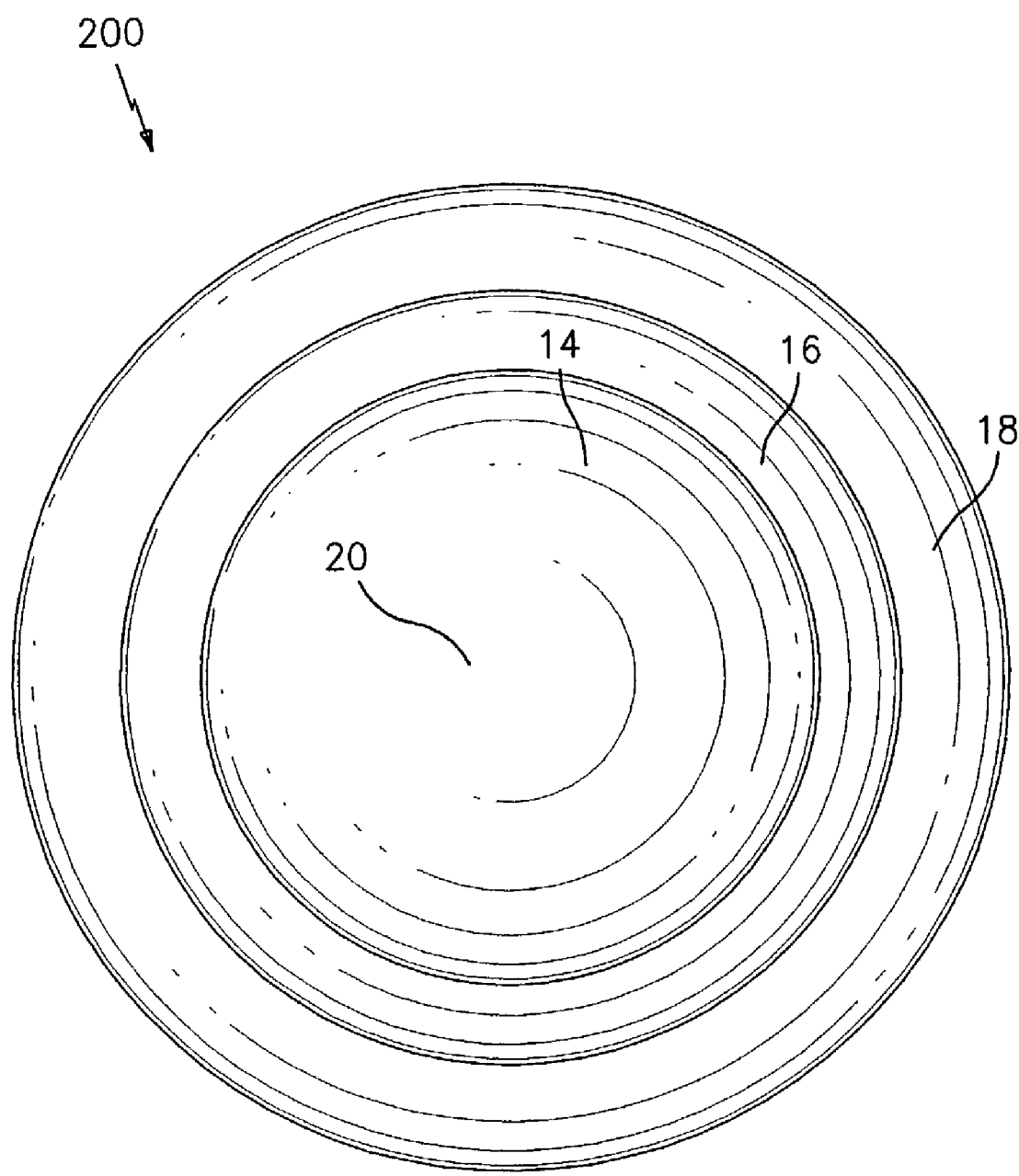
FIG. 16 is a top plan view thereof.
Figure 17:
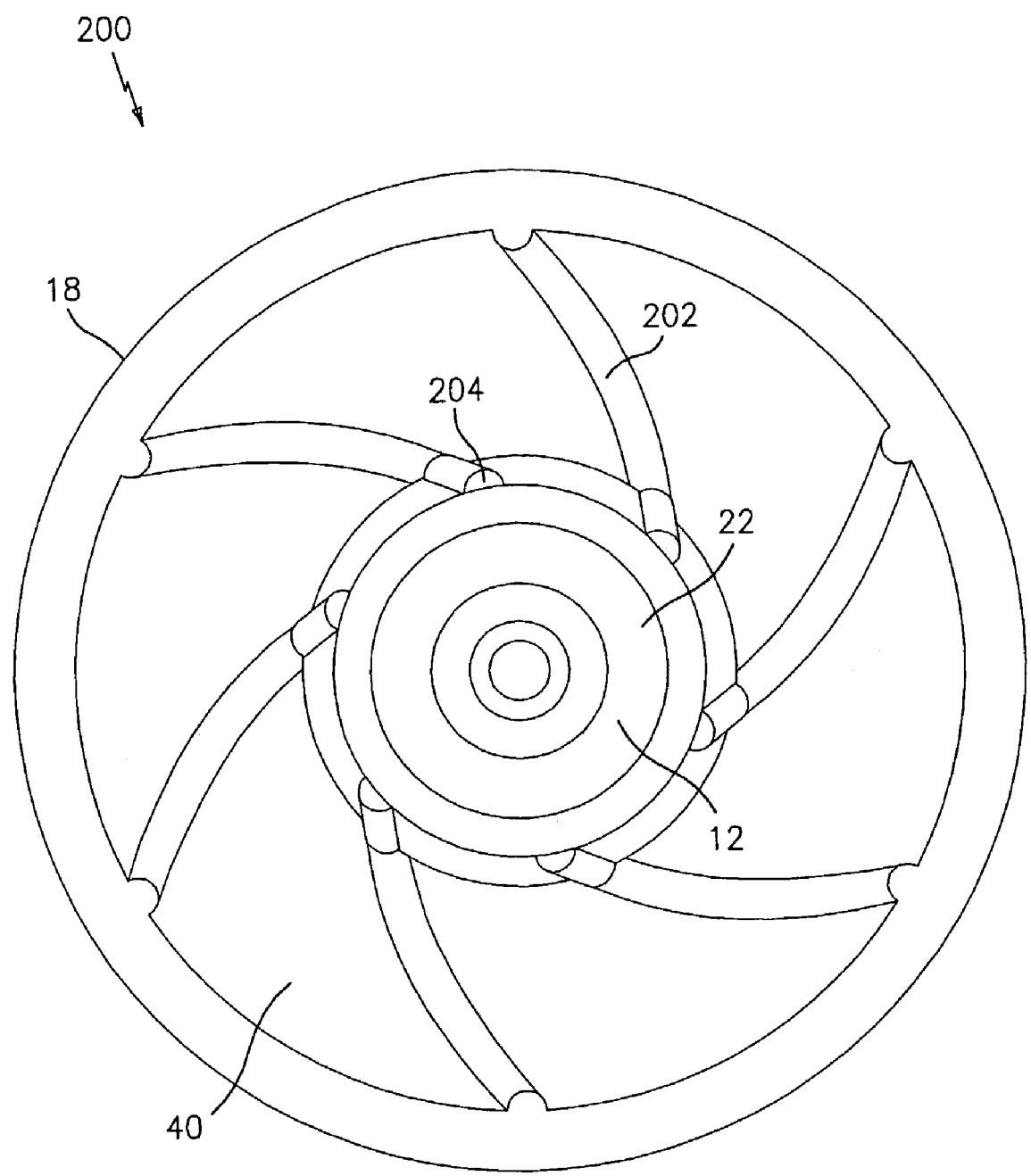
FIG. 17 is a bottom plan view thereof.
Figure 18:
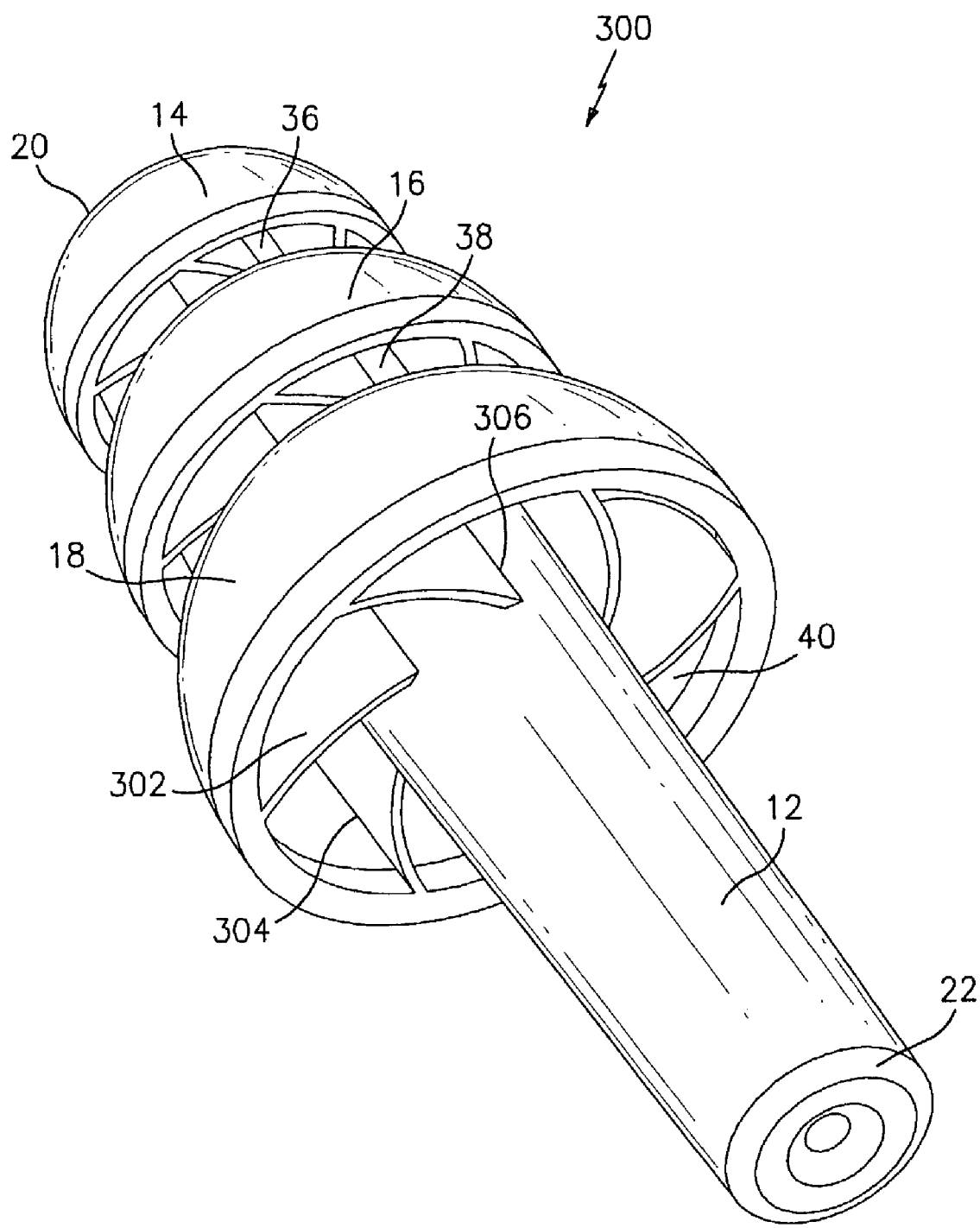
FIG. 18 is a bottom perspective view of an earplug in another embodiment of the invention.
Figure 19:
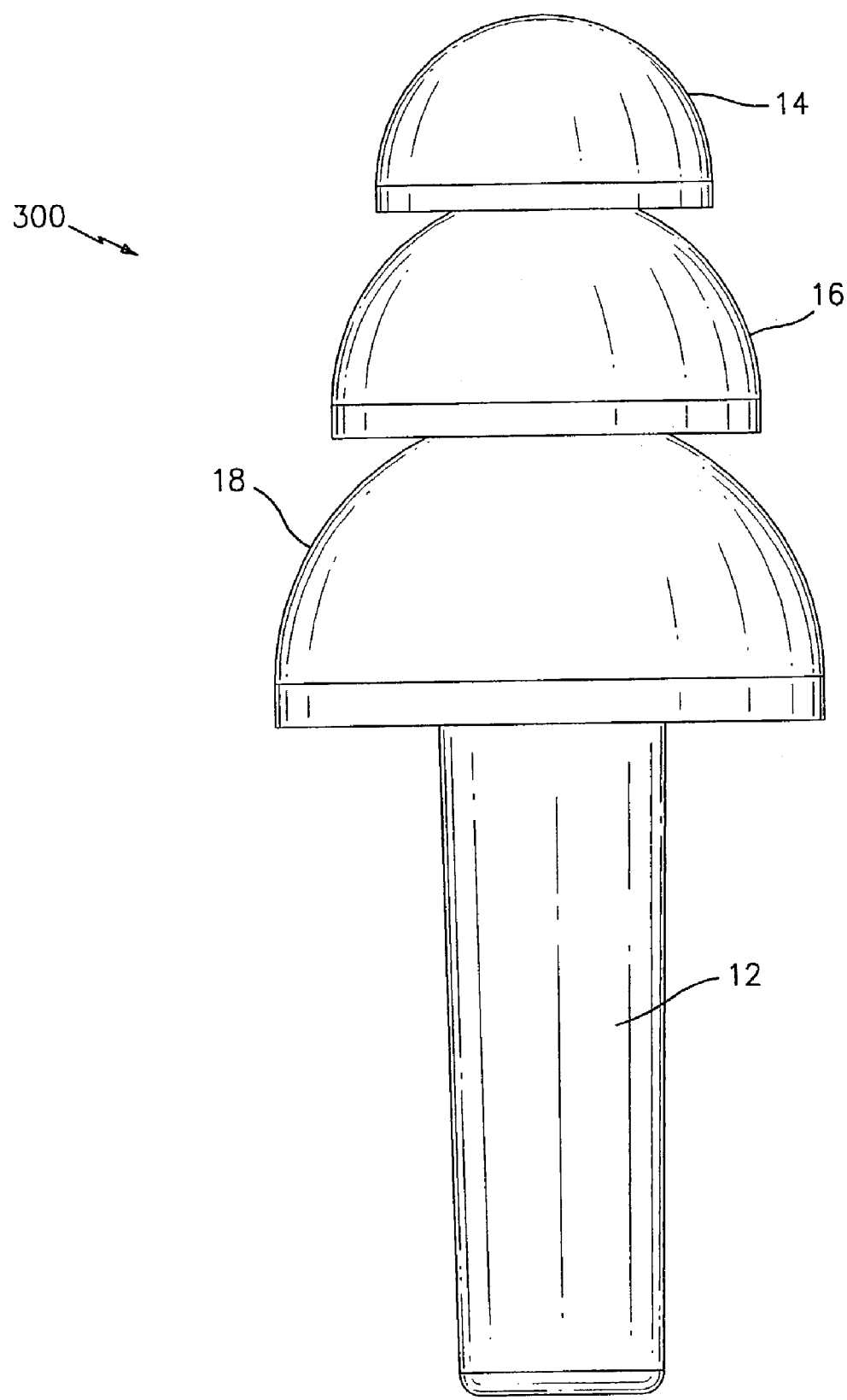
FIG. 19 is a side elevational view thereof, all other side views being mirror images thereof.
Figure 20:
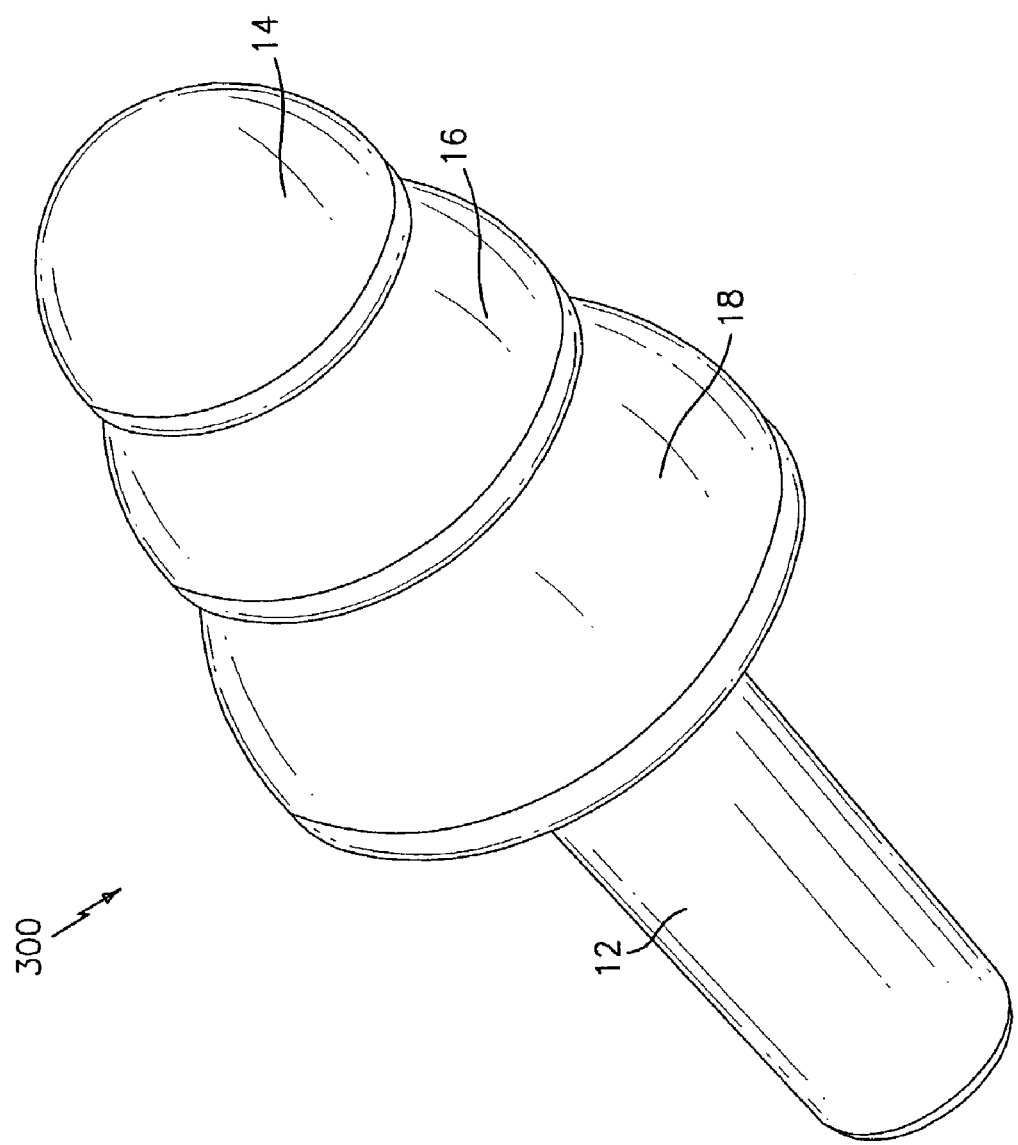
FIG. 20 is a top perspective view thereof.
Figure 21:
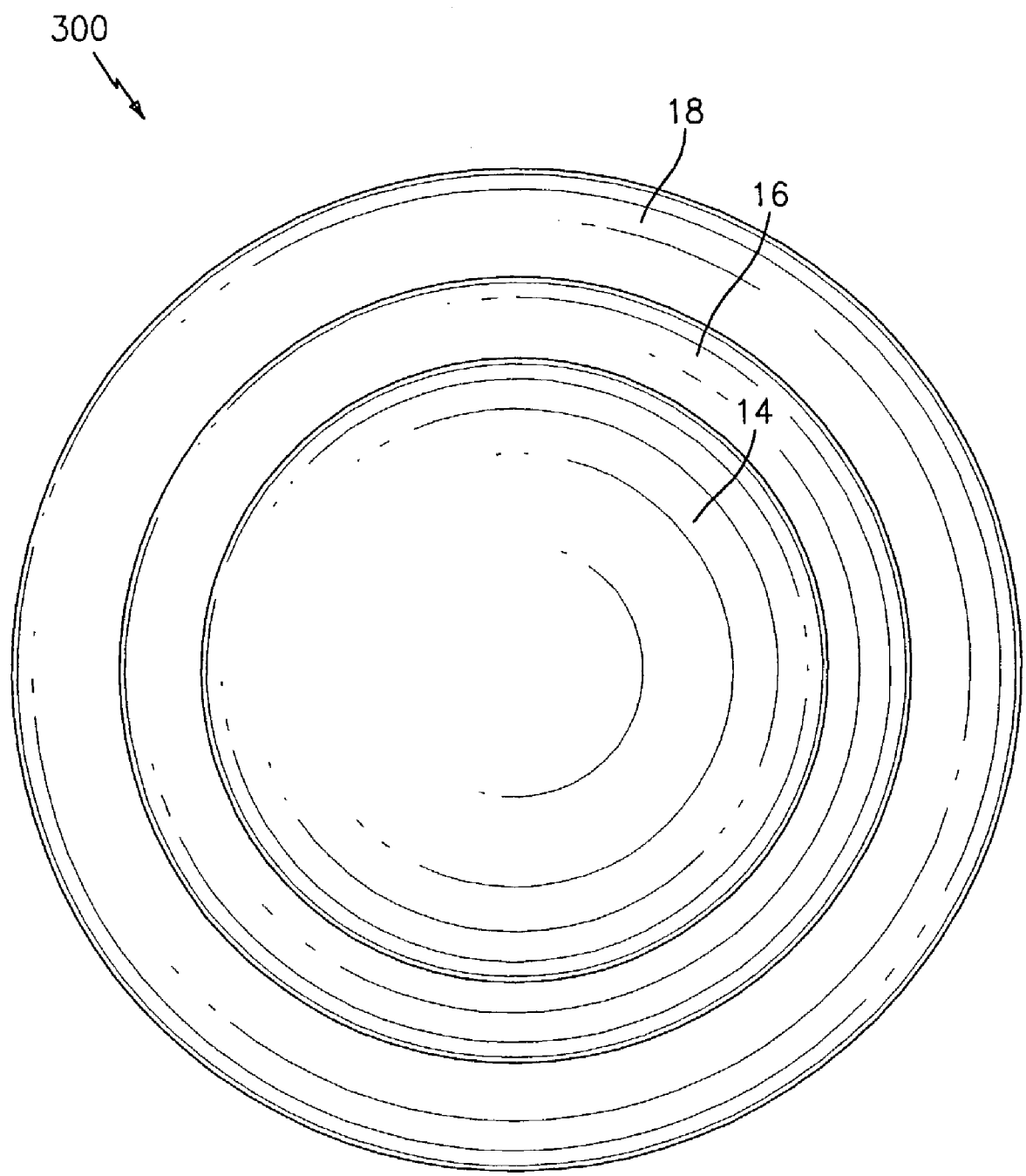
FIG. 21 is a top plan view thereof.
Figure 22:
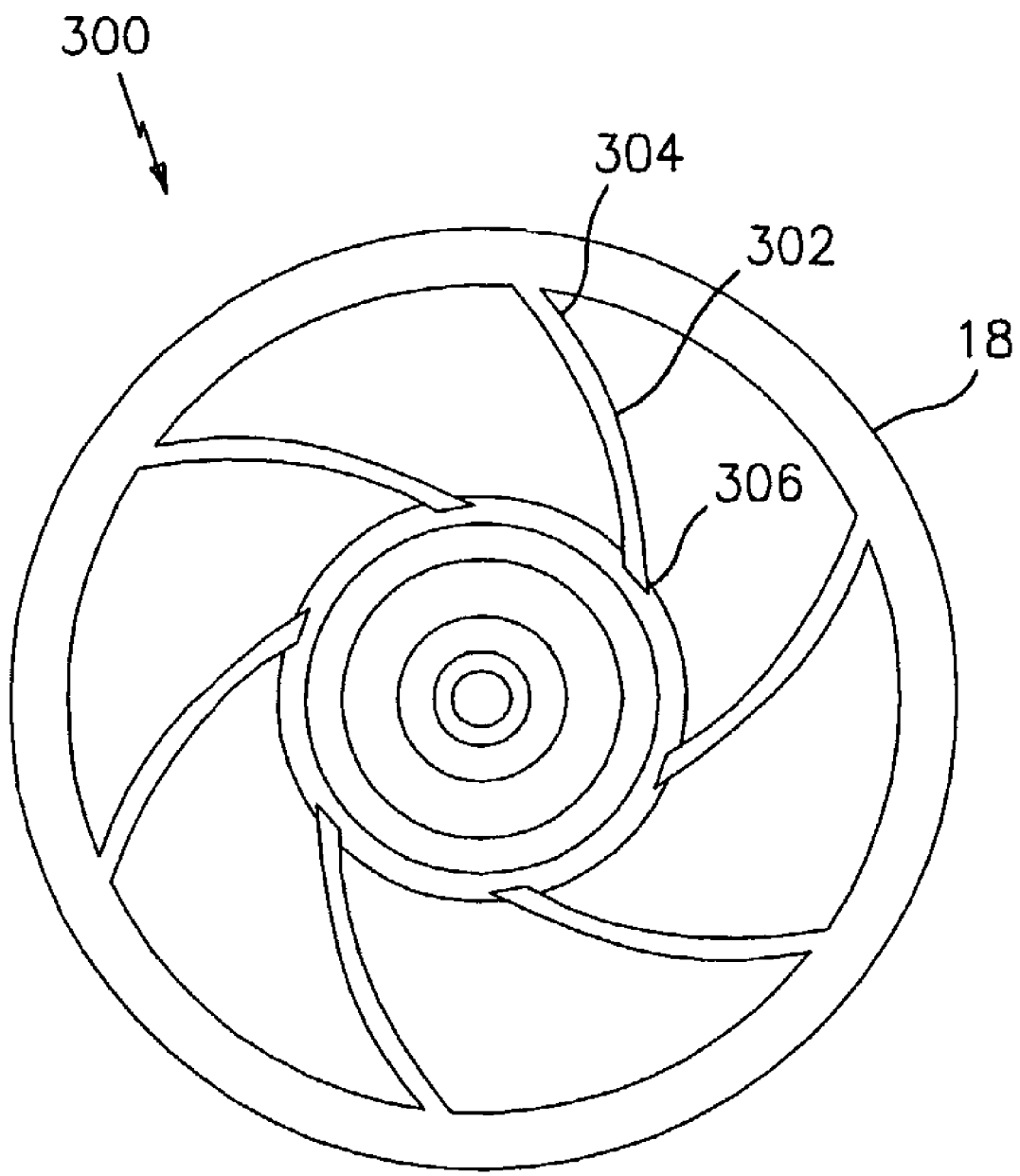
FIG. 22 is a bottom plan view thereof.

The flanges include ribs 42 formed at inner surfaces 36, 38, and 40. Ribs 42 include six individual ribs which extend the length of inner surfaces 36, 38, and 40 in a radial manner originating at stem 12 and terminating at ends of inner surfaces 36, 38, 40 proximate second end 22 of earplug 10, as best shown in FIG. 6. Ribs 42 protrude from inner surfaces 36, 38, and 40 toward stem 12; the extent of protrusion depending upon particular properties desired of earplug 10. Ribs 42 are substantially semi-circular in cross-section. Of course, ribs 42 may comprise any curvilinear or rectilinear cross-section and may be of any of a variety of sizes. Ribs 42 may be of a same material as the flanges and formed integrally therewith or ribs 42 may be of a material other than that of the flanges and bonded thereto.

Ribs 42 provide an added degree of stiffness to the flanges to prevent undesired wrinkling while at the same time allowing the flanges to compress sufficiently when the earplug is inserted in an ear to provide desired attenuation and comfort for the user.

In one embodiment, a length of earplug 10, from first end 20 to second end 22, is approximately 1.25 inches. A width of stem 12 at first end 20 is about 0.17 inches. A width of stem 12 at second end 22 is about 0.23 inches. A diameter of stem 12 is largest beneath third flange 18 where the diameter is about 0.25 inches. A length of first, second, and third flanges 14, 15, 16 is about 0.18, 0.20, and 0.26 inches, respectively. A radius of first flange 14 measured a point on a longitudinal axis of stem 12 is about 0.126–0.156 inches. A similarly measured radius of second flange 16 is about 0.170–0.200 inches and a radius of third flange 18 is about 0.220–0.255 inches. A thickness of first, second, and third flanges 14, 15, 16 is about 0.02 inches. A height of which rib 42 protrudes from inside surfaces 36, 38, 40 is approximately 0.01 inches. A diameter of cavity 13 is about 0.05–0.10. The described dimensions are exemplary and pertain to one embodiment of the invention. Of course, the invention contemplates a variety of dimensions of the particular features of the earplug.

FIGS. 7–11 show the earplug of the present invention in another embodiment generally indicated by reference numeral 100.

Like parts in the various embodiments disclosed herein are indicated by consistent reference numerals throughout. Such like parts will not be re-introduced nor re-described in detail. For description of like parts, see the introduction thereof above with reference to FIGS. 1–6.

Earplug 100 includes stem 12 and first, second and third flanges 14, 16, and 18. At inner surfaces 36, 38, and 40, earplug 100 includes ribs 42 as well as ribs 102 formed orthogonally with respect to ribs 42. That is, ribs 102 are disposed circumferentially about stem 12 while ribs 42 extend radially from stem 12. In this way, ribs 42 and 102 form a web-like arrangement on inner surfaces 36, 38, and 40.

FIGS. 12–17 depict the earplug of the present invention in another embodiment generally indicated by reference numeral 200. Earplug 200 includes ribs 202 at inner surfaces 36, 38, and 40 of first, second, and third flanges 14, 16, and 18. Ribs 202 originate at stem 12 and traverse the length of the various inner surfaces 36, 38, 40 toward second end 22 of earplug 10 in a spiral manner. That is, ribs 202 wind helically across the inner surfaces 36, 38, 40 with respect to a longitudinal axis of stem 12. Ribs 202 protrude towards stem 12, as do ribs 42 (see description above), and may have any suitable curvilinear (as shown) or rectilinear cross-sectional shape.

Earplug 200 further includes ribs 204 disposed on stem 12 extending from second end 22 to first end 20. Ribs 204 are disposed slightly angled with respect to a longitudinal axis of stem 12, as ribs 204 traverse from second end 22 to first end 20. Thus, ribs 204 form a spiral pattern on an outer surface of the stem 12. Ribs 204 protrude radially from stem 12 in a direction toward the flanges and may have any suitable curvilinear (as shown) or rectilinear cross-sectional shape.

FIGS. 18–22 depict the earplug of the present invention in a further embodiment generally indicated by reference numeral 300.

Earplug 300 includes support flanges 302 disposed in the annular spaces respectively formed between stem 12 and first, second, and third flanges 14, 16, and 18, respectively. Support flanges 302 include first sides 304 connected to inside surfaces 36, 38, and 40. First sides 304 traverse a curved path along inside surfaces 36, 38, 40 from stem 12 to an end of the respective flange 14, 16, 18 proximate second end 22. Support flanges 302 further include second ends 306 connected to stem 12. Second ends 306 traverse stem 12 in a direction parallel to a longitudinal axis of stem 12. In this way, support flanges 302 radiate outwardly from stem 12 in a spiral configuration contacting inside surfaces 36, 38, 40 of respective flanges 14, 16, 18 at first sides 304 and contacting stem 12 at seconds sides 306.

Referring now to FIGS. 23–28 showing cross-sectional views of various embodiments of the earplug of the invention.

Figure 23:
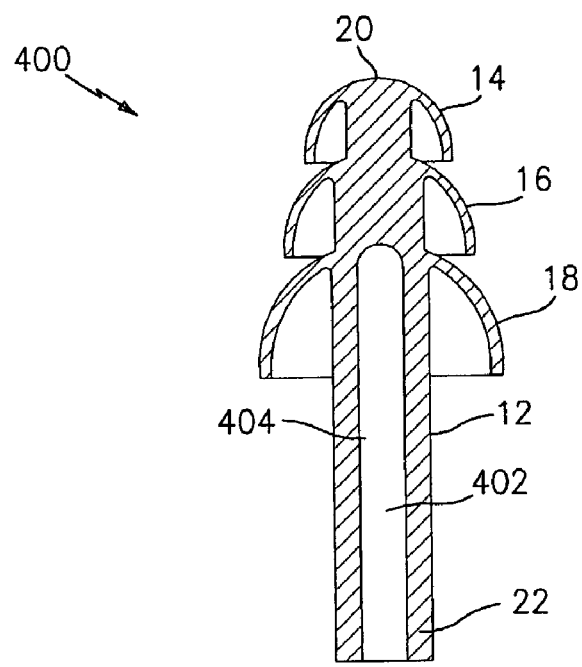
FIGS. 23–28 are cross-sectional views of earplugs in other embodiments of the invention.

FIG. 23 shows a sectional view of an embodiment of the invention indicated generally by reference numeral 400. Earplug 400 includes stem 12 and flanges 14, 16, and 18 formed thereabout, as described hereinabove. Earplug 400 further includes a cavity 402 formed in stem 12 extending longitudinally from second end 22 towards first end 20 and terminating at a point where third flange 18 connects to stem 12. A diameter to length ratio of cavity 402 is 1:9 whereas other embodiments, such as that shown in FIG. 3a, include a diameter to length ratio of 1:12. For example, a diameter of cavity 402 may be 0.1 inches and a length may be 0.9 inches. This increased size enables earplug 400 to be fitted with a component 404 of a larger size and/or different shape than component 15 discussed previously in order to extend, for example, further into the plug and to provide increased stiffness thereof.

Figure 24:
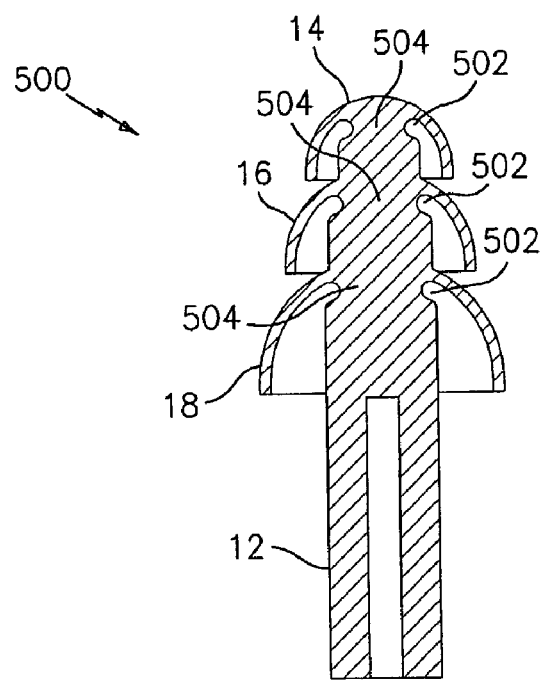
Figure 25:
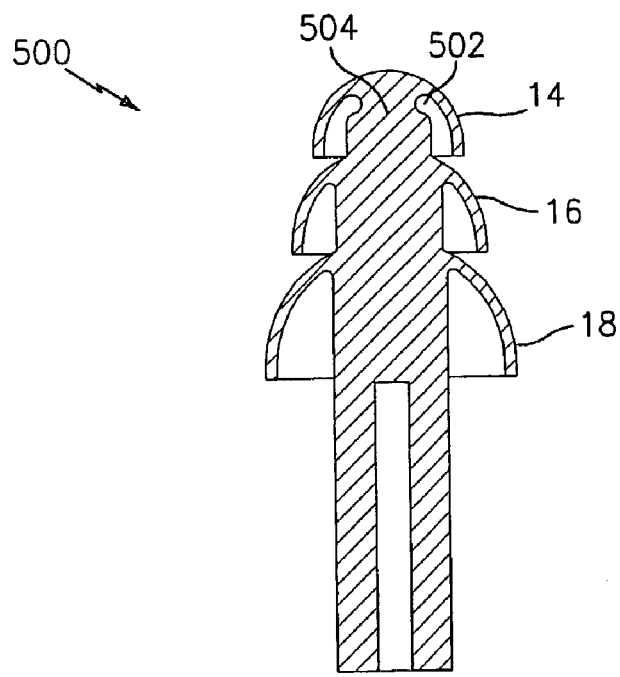
Figure 26:
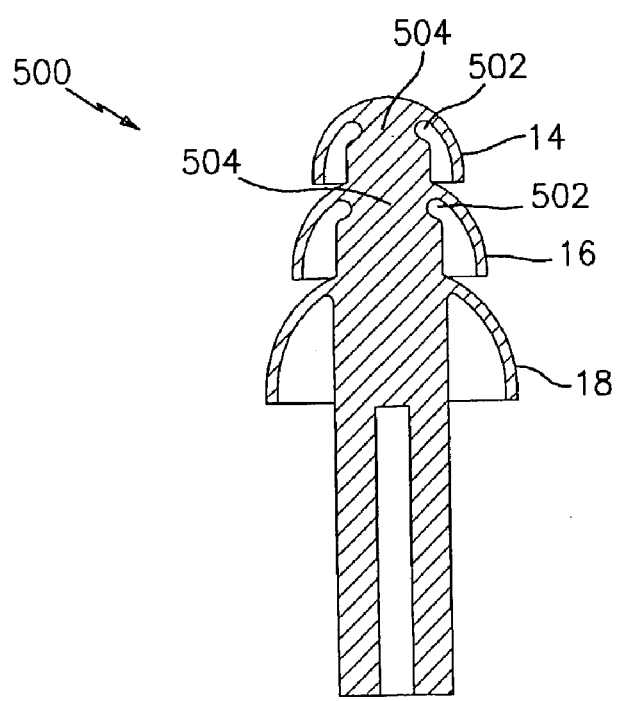

FIGS. 24–26 depict the earplug of the invention in another embodiment generally indicated by reference numeral 500. Earplug 500 includes at least one annular recessed portion 502 formed in stem 12 immediately adjacent a point 504 where the various flanges 14, 16, and 18 attach to stem 12, such that annular recessed portions 502 are formed beneath the respective flanges 14, 16, and/or 18 as shown. Annular recessed portions 502 are curvilinear in cross-section, as shown, or, alternatively, annular recessed portions 502 may be of any shape as desired.

In FIG. 24, earplug 500 includes three annular recessed portions 502 formed at points 504 beneath each first, second, and third flanges 14, 16, and 18. FIG. 25 shows earplug 500 having one annular recessed portion 502 at point 504 beneath first flange 14. In FIG. 26, earplug 500 is depicted with two annular recessed portions 502 formed at points 504 beneath first and second flanges 14 and 16.

Figure 27:
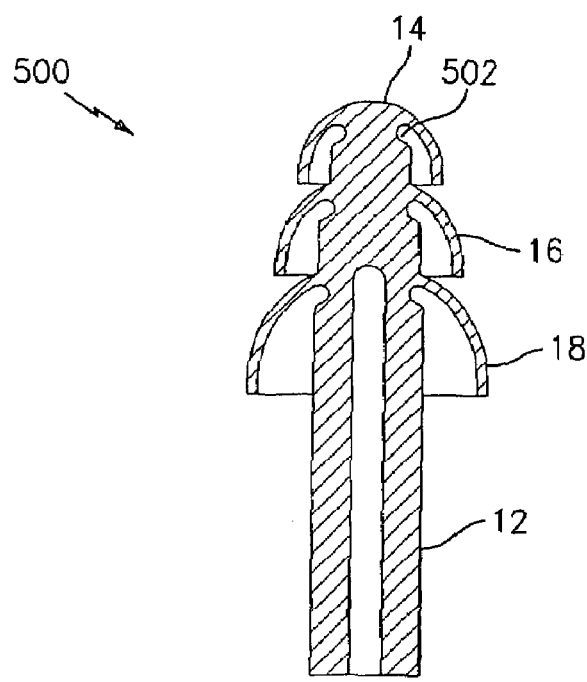
Figure 28:
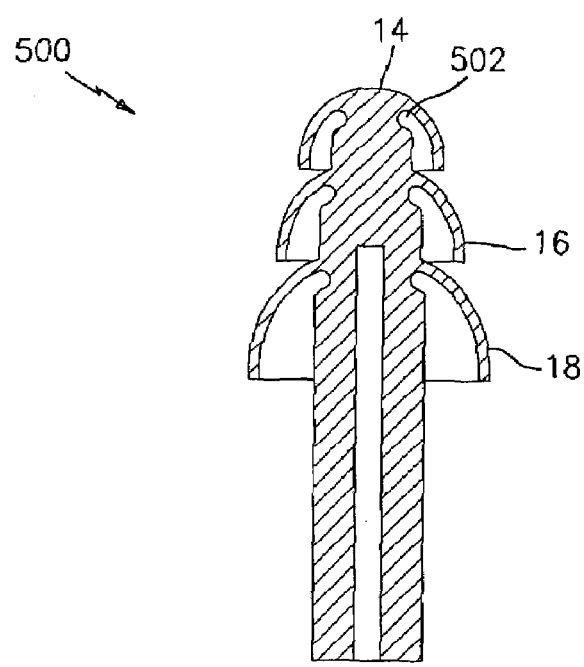

FIGS. 27 and 28 represent earplug 500 as shown in FIG. 24 having a longer and thinner cavity 506, thus adapting earplug 500 to receive different shaped and sized component members.

Annular recessed portions 502 enable stem 12 of earplug 500 to pivot slightly at the annular recessed portions during insertion of earplug 500 into an ear canal of a user. This provides for a better fitting earplug thus resulting in enhanced comfort and heightened attenuation performance.

It is understood that the diameter of stem 12 is variable and may assume a range of different sizes depending upon the particular effect sought and upon the particular component sought to be received with in stem 12. Further, the various first, second, and third portions 24, 26, and 28 of stem 12 may be sized, in diameter and in length, variously with respect to one another.

Similarly, the component received within stem 12 may comprise various diameters and lengths to provide the earplug with the effect desired. As mentioned, the component includes, among other elements, a rigid or semi-rigid insert and a cord.

While annular recessed portions 502 have been described as being formed at point 504 beneath the flanges and adjacent to the portion of the flanges which attach to stem 12, it will be appreciated that annular recessed portions 502 may be formed at any of a plurality of positions along stem 12. Additionally, more and less than the three annular recessed portions 502, discussed hereinabove, are contemplated within the scope of the invention and may be utilized in further embodiments.

The earplug of the invention can be fabricated by any suitable polymer molding technique, such as by injection molding thereof. The flanges may be made of any suitable resilient polymeric material. The component member can, of course, be composed of a resilient polymeric material of the same type employed for the flanges or, if desired, can be composed of a resilient polymeric material having a somewhat higher Shore A Durometer hardness value.

Obviously, there are many known resilient polymeric materials which may be utilized effectively in the fabrication of the earplugs of the invention. For instance, natural rubber, neoprene rubber, SBR rubber, silicone rubber, EPDM rubber, polybutadiene rubber, polyurethane elastomers, ethylene vinyl acetate elastomers, elastomers based on acrylic acid precursors and vinyl halide polymers are all generally suitable materials of construction which can generally be procured from commercial sources with the necessary Shore A Durometer values or which can be suitably compounded (such as by internal and/or external plasticizing thereof) so as to confer the necessary hardness values thereto. Preferably, a thermoplastic elastomer (TPE) is used to form the earplug. Any of a number of commercially available TPEs may be utilized.

The hearing protection device described herein provides a flanged resilient polymeric stemmed earplug in which wrinkling of the flanges upon insertion into an ear canal is reduced and yet comfort, good attenuation, and ease of use is maintained. These advantages are obtained by particular sizing of the earplug, by rib and flange arrangements provided on various surfaces of the plugs, and/or by annular recessed portions formed at various locations along the stem of the plug.

While the invention is described above with reference to a preferred embodiment, it will be understood by those skilled in the art that various changes may be made and equivalents substituted without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the present description.

The invention claimed is:

1. An earplug, comprising:
   an elongate stem component having a first end and an opposite second end;
   a first flange disposed on the stem proximate the first end;
   a second flange disposed on the stem adjacent the first flange;
   a third flange disposed on the stem adjacent the second flange, opposite the first flange, and proximate the second end;
   a rib support element formed on the first, second, and third flanges;
   wherein, the first, second, and third flanges comprise generally hemispherical flange elements extending from the stem in a direction toward the second end such that generally annular spaces are formed between inner surfaces of the first, second, and third flanges and the stem, and wherein the rib support element is formed on the inner surfaces.

2. The earplug of claim 1, wherein the first, second, and third flanges are formed of a resilient polymeric material and wherein the rib support element comprises a protrusion extending from each of the inner surfaces, the protrusion being composed of the resilient polymeric material and formed integrally with the first, second, and third flanges.

3. The earplug of claim 1, wherein the rib support element comprises a plurality of elongated protrusions extending from the stem across each of the inner surfaces in a direction toward the second end such that the plurality of elongated protrusions are substantially parallel with a longitudinal axis of the stem.

4. The earplug of claim 3, wherein the plurality of protrusions comprises six protrusions spaced about sixty degrees apart about each of the generally hemispherical flange elements.

5. The earplug of claim 3, wherein the rib support element further comprises a plurality of annular protrusions extending about each of the inner surfaces in a direction perpendicular to the longitudinal axis of the stem so as to perpendicularly intersect the plurality of elongated protrusions.

6. The earplug of claim 5, wherein the plurality of elongated protrusions comprises six elongated protrusions extending from the stem along the inner surfaces, adjacent elongated protrusions being spaced about sixty degrees apart, and wherein the plurality of annular protrusions comprises two annular protrusions formed on the inner surfaces encircling the stem.

7. The earplug of claim 1, wherein the rib support element comprises a plurality of spiral protrusions extending from the stem helically across the inner surfaces in a direction toward the second end.

8. The earplug of claim 7, wherein the plurality of spiral protrusions comprises six protrusions extending helically from the stem across the inner surfaces.

9. The earplug of claim 7, wherein the rib support element further comprises a plurality of stem protrusions formed on the stem and each extending from the first end to the second end.

10. The earplug of claim 9, wherein the plurality of stem protrusions comprise six stem protrusions formed on the stem at an angle with a longitudinal axis of the stem such that the six stem protrusions are not parallel with the longitudinal axis of the stem.

11. The earplug of claim 10, wherein the plurality of spiral protrusions comprises six spiral protrusions corresponding to the six stem protrusions, and wherein an end of each of the six spiral protrusions contacts an end of each of the respective six stem protrusions at points where the first, second, and third flanges contact the stem.

12. The earplug of claim 1, wherein the rib support element comprises a plurality of support flanges extending from the inner surfaces, through the annular spaces, to the stem so as to radially connect the first, second, and third flanges to the stem.

13. The earplug of claim 12, wherein the support flanges extend helically from the stem to meet the inner surfaces.

14. The earplug of claim 12, wherein the plurality of support flanges comprises six support flanges, each support flange including a first support flange side disposed on the stem in a direction parallel with a longitudinal axis of the stem and an opposite second support flange side disposed helically on the inner surface extending from the stem across the inner surface in a direction toward the second end of the stem, the support flange extending from the first support flange side to the second support flange side.

15. An earplug, comprising:
an elongate stem component having a first end and an opposite second end;
a plurality of substantially hemispherical flanges connected to the stem at respective attachment points and extending from the stem in a direction toward the second end such that respective annular spaces are formed between inner surfaces of the plurality of flanges and the stem; and
a plurality of annular recessed portions corresponding to the plurality of flanges formed circumferentially in the stem in the annular spaces proximate the attachment points.

16. The earplug of claim 15, wherein the plurality of flanges comprises a first flange, a second flange, and a third flange and wherein the plurality of annular recessed portions comprises a first portion, a second portion, and a third portion.

* * * * *